(12) United States Patent
Li

(10) Patent No.: US 11,338,022 B2
(45) Date of Patent: *May 24, 2022

(54) METHOD FOR PREVENTING AND TREATING ANGIOCARDIOPATHY

(71) Applicant: TALENGEN INTERNATIONAL LIMITED, Hong Kong (CN)

(72) Inventor: Jinan Li, Guangdong (CN)

(73) Assignee: TALENGEN INTERNATIONAL LIMITED, Hong Kong (CN)

( * ) Notice: Subject to any disclaimer, the term of this patent is extended or adjusted under 35 U.S.C. 154(b) by 228 days.

This patent is subject to a terminal disclaimer.

(21) Appl. No.: 16/063,569

(22) PCT Filed: Dec. 16, 2016

(86) PCT No.: PCT/CN2016/110453
§ 371 (c)(1),
(2) Date: Jun. 18, 2018

(87) PCT Pub. No.: WO2017/101871
PCT Pub. Date: Jun. 22, 2017

(65) Prior Publication Data
US 2019/0083586 A1    Mar. 21, 2019

(51) Int. Cl.
*A61K 38/48* (2006.01)
*C12N 9/72* (2006.01)

(52) U.S. Cl.
CPC ............ *A61K 38/484* (2013.01); *A61K 38/48* (2013.01); *C12N 9/6456* (2013.01)

(58) Field of Classification Search
CPC ............... A61K 38/484; C12N 9/6435; C12Y 304/21007; A61P 9/40; A61P 9/14; A61P 9/10
See application file for complete search history.

(56) References Cited

U.S. PATENT DOCUMENTS

| | | | |
|---|---|---|---|
| 4,996,050 A | 2/1991 | Tsukada et al. | |
| 5,637,299 A | 6/1997 | McDonagh et al. | |
| 5,776,452 A | 7/1998 | Eibl et al. | |
| 2002/0159992 A1* | 10/2002 | Henkin ......... | C12Y 304/21007 424/94.63 |
| 2003/0026798 A1 | 2/2003 | Zimmerman et al. | |
| 2003/0180934 A1 | 9/2003 | Ni et al. | |
| 2005/0250694 A1 | 11/2005 | Ma | |
| 2007/0196350 A1 | 8/2007 | Bartels | |
| 2009/0208448 A1 | 8/2009 | Solomon et al. | |
| 2019/0247472 A1 | 8/2019 | Li | |
| 2020/0023043 A1 | 1/2020 | Blackman et al. | |

FOREIGN PATENT DOCUMENTS

| | | |
|---|---|---|
| CA | 2145841 A1 | 10/1995 |
| CA | 2475277 A1 | 8/2003 |
| CA | 2474947 A1 | 11/2003 |
| CA | 2662083 A1 | 3/2008 |
| CA | 2707266 A1 | 6/2009 |
| CA | 2823491 A1 | 7/2012 |
| CA | 2844644 A1 | 2/2013 |
| CA | 2888996 A1 | 5/2014 |
| CA | 3002915 A1 | 5/2017 |
| CA | 3047172 A1 | 6/2018 |
| CA | 3047176 A1 | 6/2018 |
| CA | 3047173 A | 6/2021 |
| CN | 1585649 A | 2/2005 |
| CN | 1191856 C | 3/2005 |
| CN | 1643140 A | 7/2005 |
| CN | 1768138 A | 5/2006 |
| CN | 1856319 A | 11/2006 |
| CN | 1961958 A | 5/2007 |
| CN | 101002888 A | 7/2007 |
| CN | 101573134 A | 11/2009 |
| CN | 101918548 A | 12/2010 |
| CN | 102121023 A | 7/2011 |
| CN | 102154253 A | 8/2011 |
| CN | 102482338 | 5/2012 |
| CN | 102872020 A | 1/2013 |
| CN | 103384722 A | 11/2013 |
| CN | 103764163 A | 4/2014 |
| CN | 104789544 A | 7/2015 |
| CN | 105008323 A | 10/2015 |
| CN | 105705520 A | 6/2016 |
| EP | 0307847 | 3/1989 |
| EP | 0674906 A2 | 10/1995 |
| EP | 2201946 A1 | 6/2010 |
| EP | 3395360 A1 | 10/2018 |
| EP | 3556383 A1 | 10/2019 |
| EP | 3556384 A1 | 10/2019 |
| EP | 3556390 A1 | 10/2019 |

(Continued)

OTHER PUBLICATIONS

UniProtKB "P00747(PLMN_HUMAN)" 14 pages, accessed Jun. 20, 2020 (Year: 2020).*
Results from USPTO Sequence Search in the UniProtKB database "Result 1 PLMN_HUMAN" performed Apr. 27, 2020, 7 pages (Year: 2020).*
Mayo Clinic "Heart failure" 1998-2020, 6 pages (Year: 1998).*
Science Daily "How Diabetes Drives Atherosclerosis" 3 pages, 2008 (Year: 2008).*
Alexander CM and Werb, Z. (1991) Extracellular matrix degradation. In Cell Biology of Extracellular Matrix, Hay ED, ed. (New York: Plenum Press), pp. 255-302.

(Continued)

*Primary Examiner* — Thane Underdahl

(74) *Attorney, Agent, or Firm* — Hauptman Ham, LLP

(57) ABSTRACT

The present invention relates to the effect of plasminogen in the treatment and/or elimination of angiocardiopathy, especially angiocardiopathy caused by diabetes mellitus, thereby providing a new strategy for treating different kinds of angiocardiopathy, especially angiocardiopathy and its related disorders caused by diabetes mellitus.

6 Claims, 9 Drawing Sheets

Specification includes a Sequence Listing.

(56) References Cited

FOREIGN PATENT DOCUMENTS

| | | |
|---|---|---|
| EP | 3556391 A1 | 10/2019 |
| JP | 2002510209 A | 4/2002 |
| JP | 2019-500422 A | 1/2019 |
| JP | 2020502140 A | 1/2020 |
| JP | 2020502150 A | 1/2020 |
| JP | 2020502151 A | 1/2020 |
| JP | 2020510628 A | 4/2020 |
| TW | 200803890 A1 | 1/2008 |
| TW | 201625294 A | 7/2016 |
| TW | 201822800 A | 7/2018 |
| TW | 201822801 A | 7/2018 |
| TW | 201822802 A | 7/2018 |
| TW | 201822803 A | 7/2018 |
| TW | 201822804 A | 7/2018 |
| TW | 201822807 A | 7/2018 |
| TW | 201822808 A | 7/2018 |
| TW | I644682 B | 12/2018 |
| TW | I669130 B | 8/2019 |
| WO | 95/12407 A1 | 5/1995 |
| WO | 99/00420 A1 | 1/1999 |
| WO | 0018436 A1 | 4/2000 |
| WO | 03/020297 A2 | 3/2003 |
| WO | 03020297 A2 | 3/2003 |
| WO | 03033019 A2 | 4/2003 |
| WO | 2006122249 A2 | 11/2006 |
| WO | 2007101005 A2 | 9/2007 |
| WO | 2008/026999 A2 | 3/2008 |
| WO | 2010125148 A2 | 11/2010 |
| WO | 2014/070983 A1 | 5/2014 |
| WO | 2015/023752 A1 | 2/2015 |
| WO | 2017/077380 A1 | 5/2017 |
| WO | 00/18436 A1 | 4/2020 |

OTHER PUBLICATIONS

Werb, Z., Mainardi, C.L., Vater, C.A., and Harris, E.D., Jr. (1977). Endogenous activiation of latent collagenase by rheumatoid synovial cells. Evidence for a role of plasminogen activator. N. Engl. J. Med. 296, 1017-1023.

He, C.S., Wilhelm, S.M., Pentland, A.P., Marmer, B.L., Grant, G.A., Eisen, A.Z., and Goldberg, G.I. (1989). Tissue cooperation in a proteolytic cascade activating human interstitial collagenase. Proc. Natl. Acad. Sci. U. S. A 86, 2632-2636.

Stoppelli, M.P., Corti, A., Soffientini, A., Cassani, G., Blasi, F., and Assoian, R.K. (1985). Differentiation-enhanced binding of the aminoterminal fragment of human urokinase plasminogen activator to a specific receptor on U937 monocytes. Proc. Natl. Acad. Sci. U. S. A 82, 4939-4943.

Vassalli, J.D., Baccino, D., and Belin, D. (1985). A cellular binding site for the Mr 55, 000 form of the human plasminogen activator, urokinase. J. Cell Biol. 100, 86-92.

Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

Saksela, O. and Rifkin, D.B. (1988) Cell-associated plasminogen activation: regulation and physiological functions. Annu. Rev. Cell Biol. 4, 93-126.

Raum, D., Marcus, D., Alper, C.A., Levey, R., Taylor, P.D., and Starzl, T.E. (1980) Synthesis of human plasminogen by the liver. Science 208, 1036-1037.

Wallén P (1980). Biochemistry of plasminogen. In Fibrinolysis, Kline DL and Reddy KKN, eds. (Florida: CRC.

Sottrup-Jensen, L., Zajdel, M., Claeys, H., Petersen, T.E., and Magnusson, S. (1975). Amino-acid sequence of activation cleavage site in plasminogen: homology with "pro" part of prothrombin. Proc. Natl. Acad. Sci. U. S. A 72, 2577-2581.

Collen, D. and Lijnen, H.R. (1991). Basic and clinical aspects of fibrinolysis and thrombolysis. Blood 78, 3114-3124.

Alexander, C.M. and Werb, Z. (1989). Proteinases and extracellular matrix remodeling. Curr. Opin. Cell Biol. 1, 974-982.

Mignatti, P. and Rifkin, D.B. (1993). Biology and biochemistry of proteinases in tumor invasion. Physiol Rev. 73, 161-195.

Collen, D. (2001). Ham-Wasserman lecture: role of the plasminogen system in fibrin-homeostasis and tissue remodeling. Hematology. (Am. Soc. Hematol. Educ. Program. ) 1-9.

Rifkin, D.B., Moscatelli, D., Bizik, J., Quarto, N., Biei, F., Dennis, P., Flaumenhaft, R., and Mignatti, P. (1990). Growth factor control of extracellular proteolysis. Cell Differ. Dev. 32, 313-318.

Andreasen, P.A., Kjoller, L., Christensen, L., and Duffy, M.J. (1997). The urokinase-type plasminogen activator system in cancer metastasis: a review. Int. J. Cancer 72, 1-22.

Rifkin, D.B., Mazzieri, R., Munger, J.S., Noguera, I., and Sung, J. (1999). Proteolytic control of growth factor availability. APMIS 107, 80-85.

Marder V J, Novokhatny V. Direct fibrinolytic agents: biochemical attributes, preclinical foundation and clinical potential [J]. Journal of Thrombosis and Haemostasis, 2010, 8(3): 433-444.

Hunt J A, Petteway Jr S R, Scuderi P, et al. Simplified recombinant plasmin: production and fu-nctional comparison of a novel thrombolytic molecule with plasma-derived plasmin [J]. Thromb Haemost, 2008, 100(3): 413-419.

Sottrup-Jensen L, Claeys H, Zajdel M, et al. The primary structure of human plasminogen: Isolation of two lysine-binding fragments and one "mini"-plasminogen (MW, 38, 000) by elastase-catalyzedspecific limited proteolysis [J]. Progress in chemical fibrinolysis and thrombolysis, 1978, 3: 191-209.

Nagai N, Demarsin E, Van Hoef B, et al. Recombinant human microplasmin: production and potential therapeutic properties [J] Journal of Thrombosis and Haemostasis, 2003, 1(2): 307-313.

Dimitrios Davalos, Katerina Akassoglou. Fibrinogen as a key regulator of inflammation in disease. Seminars in Immunopathology,2012. 34(1):43-62.

Valvi D, Mannino DM, Mullerova H, et al. Fibrinogen, chronic obstructive pulmonary disease (COPD) and outcomes in two United States cohorts. Int J Chron Obstruct Pulmon Dis 2012;7:173-82.

R. Langhorn and J.L. Willesen. Cardiac Troponins in Dogs and Cats. J Vet Intern Med 2016;30:36-50.

Moungjaroen J, Nimmannit U, Callery PS, Wang L, Azad N, Lipipun V, Chanvorachote P, Rojanasakul Y (2006). Reactive oxygen species mediate caspase activation and apoptosis induced by lipoic acid in human lung epithelial cancer cells through Bcl-2 downregulation. J Pharmacol Exp Ther 319, 1062-1069.

Wang L, Chanvorachote P, Toledo D, Stehlik C, Mercer RR, Castranova V, Rojanasakul Y (2008). Peroxide is a key mediator of Bcl-2 down-regulation and apoptosis induction by cisplatin in human lung cancer cells. Mol Pharmacol 73, 119-127.

S.R. Chaplan et al.Quantitative assessment of tactile allodynia in the rat paw, Journal of Neuroscience Methods 53 (1994) 55-63.

Zwart B, Ciurana C, Rensink I, Manoe R, Hack CE, et al. (2004) Complement activation by apoptotic cells occurs predominantly via IgM and is limited to late apoptotic (secondary necrotic) cells. Autoimmunity 37: 95-102.

Zhang M, Takahashi K, Alicot EM, Vorup-Jensen T, Kessler B, et al. (2006) Activation of the lectin pathway by natural IgM in a model of ischemia/ reperfusion injury J Immunol 177: 4727-4734.

Kim SJ, Gershov D, Ma X, Brot N, Elkon KB (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

Karmen A, Wroblewski F, Ladue JS (Jan. 1955). Transaminase activity in human blood. The Journal of Clinical Investigation. 34 (1): 126-31.

Wang CS, Chang I I, Yao WJ, Wang ST, Chou P (Apr. 2012). Impact of increasing alanine aminotransferase levels within normal range on incident diabetes. Journal of the Formosan Medical Association = Taiwan Yi Zhi. 111 (4): 201-8.

Zhang, Yue et al.. Fibrinolytic System and the Macro-Vascular Complications in Type 2 Diabetes Mellitus, Section of Endocrinology Foreign Medical Sciences, vol. 25, Apr. 30, 2005.

International Search Report dated Mar. 3, 2017 from corresponding application No. PCT/CN2016/110453.

(56) References Cited

OTHER PUBLICATIONS

TW Office Action with English translation from corresponding application No. TW 105141900.
Plow, E.F. et al., "The Functions of Plasminogen in Cardiovascular Disease". Trends Cardiovasc Med., vol. 14, No. 5, Jul. 31, 2004, pp. 180-186.
Yang, Lin-hua et al., "Changes of Fbrinolytic Parameters in Coronary Heart Disease", Chinese Journal of Thrombosis and Hemostasis, 2004, vol. 10, No. 1, pp. 8-10.
Xu Dongjuan et al., "Therapeutic effect of recombinant tissue plasminogen activator on acute cerebral infarction", Prevention and Treatment of Cerebral-Vascular Disease, Feb. 2012, vol. 12, No. 1, pp. 37-39.
Brazionis, Laima et al., "Plasminogen Activator Inhibitor-1 Activity in Type 2 Diabetes: A Different Relationship With Coronary Heart Disease and Diabetic Retinopathy", Arterioscler Thromb Vase Biol, vol. 28, Jan. 31, 2008, pp. 786-791.
Ajjan, R.A. et al., "Diabetes is associated with posttranslational modifications in plasminogen resulting in reduced plasmin generation and enzyme-specific activity", Blood, vol. 122(1), May 22, 2013, pp. 134-142.
NP-000292.1, "plasminogen isoform 1 precursor", GenBank, Mar. 15, 2015, entire document.
Qiong, Wang, "Rest and Protection of Pancreatic Islet Beta-cell", Chinese Nursing Research, vol. 19(No. 9A), Sep. 30, 2005, pp. 1706-1708.
Ma, Li-Jun et al., "Prevention of obesity and insulin resistance in mice lacking plasminogen activator inhibitor 1", Diabetes, vol. 53(2), Feb. 1, 2004, pp. 336-346.
Miles, Lindsey A., et al., "The Plasminogen Receptor, PLG-RKT, Regulates Metabolic Homeostasis and Promotes Healthy Adipose Function", Circulation, Nov. 11, 2016, A19088, vol. 134, Issue Suppl 1.
Chang, P.C., et al., "Human plasminogen kringle 1-5 reduces atherosclerosis and neointima formation in mice by suppressing the inflammatory signaling pathway",Journal of Thrombosis and Haemostasis, vol. 8, No. 1, Jan. 1, 2010, pp. 194-201.
Abe, Takeshi, "Progress of Thrombolytic Therapy and its clinical Effect", Blood and vessel, vol. 12, No. 4, 1981, pp. 193-501.
Naito, Gen, "The Formulation and Clinical Experience of Plasminogen Activator System", Journal of Japan Society of Blood Transfusion, vol. 32 , No. 6, 1986, pp. 590-593.
Nanada Isamu, "Effect of urokinase on heart and brain infarctions combined with diabetic patients", Clinical and Yesearch, vol. 58 No. 2, 1981, pp. 659-665.
Zhou Hanming, "Fibrinolytic Enzyme Assisted Therapy for 62 Cases of Type 2 Diabetes Mellitus", Herald of medicine, Aug. 2011, vol. 30, pp. 35-36.
Schott, M.D., Dorothee et al., "Therapy With a Purified Plasminogen Concentrate in an Infant With Ligneous Conjunctivitis and Homozygous Plasminogen Deficiency", The New England Jouranal of Medicine, vol. 339(23):1679-1685, Dec. 3, 1998.
Mirsky, I. Arthur, et al., "The Destruction of Glucagon, Adrenocorticotropin and Somatotropin by Human Blood Plasma", J . Clin. Invest., vol. 28, pp. 14-20, Aug. 13, 1958.
Lugea, Aurelia et al., "Pancreas Recovery Following Caerulein-induced Pancreatitis is Impaired in Plasminogen Deficient Mice", Gastroenterology, Sep. 2006; vol. 131(3), pp. 885-899.
Fisher, Elizabeth J. et al., "Displacement of Tissue Bound Plasminogen by Glucose: A possible Mechanism in the Pathogenesis of Diabetic Nephropathy", Endocrinology and Metabolism, vol. 4, Dec. 31, 1997 pp. 371-376.
Baidu Wenku, "Research progress in the pathogenesis of diabetic cardippathy (DC)", Baidu Wenku, Webpages of evidence, Apr. 26, 2011, pp. 1-8.
Feuerstein, Giora Z. et al., "Cardioprotection and Thrombolysis by Anistreplase in Anesthetized Dogs", Journal of Cardiovascular Pharmacology, 1995, vol. 25, pp. 625-633.

Siconolfi, L. B. et al., "Mice Lacking tPA, uPA, or Plasminogen Genes Showed Delayed Functional Recovery after Sciatic Nerve Crush", The Journal Neuroscience, vol. 21, pp. 4348-4355, Jun. 15, 2001 (Jun. 15, 2001).
Akassoglou, K. et al., "Tissue Plasminogen Activator-mediated Fibrinolysis Protects Against Axonal Degeneration and Demyelination after Sciatic Nerve Injury", The Journal of Cell Biology, vol. 149, pp. 1157-1166, May 29, 2000.
Gutiérrez-Fernández, A. et al., "Plasminogen Enhances Neuritogenesis on Laminin-1", J Neurosci, vol. 29, pp. 12393-12400, Oct. 7, 2009.
Hafer-Macko, MD, Charlene E. et al., "Microvascular tissue plasminogen activator is reduced in diabetic neuropathy", Neurology, 69, pp. 268-274, Jul. 17, 2007.
Zou, PhD, Tie et al., "Exogenous Tissue Plasminogen Activator Enhances Peripheral Nerve Regeneration and Function Recovery After Injury In Mice", J Neuropathol Exp Neurol, Jan. 2006, vol. 65, No. 1, p. 78-86.
Koeki, Arimura et al., "Diabetes And Peripheral Neuropathy", The Journal of the Japanese Society of Internal Medicine, vol. 98, No. 2, 2009, pp. 399-405.
Sima, Jing et al., "The effect of angiostatin on vascular leakage and VEGF expression in rat retina", FEBS Letters 564, 19-23, Mar. 23, 2004.
Zhao Yuzhang et al. "Clinical observation of plasmin in the treatment of 36 cases of progressive cerebral infarction", Journal of North Sichuan Medical Dollege, vol. 22, No. 6, Dec. 31, 2007, pp. 549-550.
Zhang Yue,et al "Relationship between fibrinolysis change and insulin resistance in type 2 diabetes mellitus with microangiopathy", Clinical Focus, Mar. 20, 2008, vol. 23, No. 6, pp. 397-399.
Liu, Chenlian, et al. "Comparision of the Affect Ofgumepiride and Metformin On Fibrinolytic Function in Patients With Newly Diagnosed Type 2 Diabetes Mellitus", Modem Hospital, vol. 12, Jul. 12, 2012, pp. 8-9.
Hou Xinping, "Effect of type 2 diabetes insulin pump therapy on glucose and lipid metabolism and plasminogen", Journal of Heze Medical College, Dec. 31, 2012, vol. 24 No.1, pp. 21-22.
Yan, Xiao-fang, et al. "Beta cell function in relation to plasminogen activator inhibitor-1 and tissue-plasminogen activator in postmenopausal females with different glucose tolerance", Chin J Hypertens, Nov. 21, 2013, vol. 21 No. 11, pp. 1045-1048.
Polat, Sefika Burcak et al. "Evaluation of Serum Fibrinogen, Plasminogen,α2-Anti-Plasmin, and Plasminogen Activator Inhibitor Levels (PAI) and Their Correlation with Presence of Retinopathy in Patients with Type 1 DM", Journal of Diabetes Research, 2014, pp. 1-6.
Auwerx, Johan et al., "Tissue-type plasminogen activator antigen and plasminogen activator inhibitor in diabetes mellitus". Arteriosclerosis, Thrombosis, and Vascular Biology, vol. 8, Jan./Feb. 1988, p. 68-72.
Shen, Yue et al., "Plasminogen is a key proinflammatory regulator that accelerates the healing of acute and diabetic wounds", Blood, Jun. 14, 2012, vol. 119, No. 24, pp. 5879-5887.
Arenillas, MD, Juan F. et al., "Angiogenesis in Symptomatic Intracranial Atherosclerosis Predominance of the Inhibitor Endostatin Is Related to a Greater Extent and Risk of Recurrence", downloaded from http://ahajournals.org on Aug. 18, 2020; pp. 92-97.
Gonzalez, MD, Nestor R., "Antiangiogenesis and Medical Therapy Failure in Intracranial Atherosclerosis", Angiogenesis. Feb. 2018; vol. 21(1): pp. 1-27.
Zhongming, Fu, et al.; Effects of Plasmin Capsules On Antioxidation and Endothelial Function in Patientswith High Altitude Polycythemia, Journal of High Altitude Medicine, 2002, vol. 1, No. 4, pp. 33-35.
Pinkney, Jonathan H, et al.; Endothelial Dysfunction: Cause of the Insulin Resistance Syndrome, Diabetes, Sep. 1997, vol. 46, S9-13.
Robertson; R. Paul, et al.; Pancreatic islet b-cell and oxidative stress: The importance of glutathione peroxidase, FEBS Letters 581 (2007), pp. 3743-3748.
Kremen, Michal, et al.; Plasminogen mediates the atherogenic effects of macrophage-expressed urokinase and accelerates atherosclerosis in apoE-knockout mice; PNAS, Nov. 4, 2008; vol. 105, No. 44; pp. 17109-17114.

(56) References Cited

OTHER PUBLICATIONS

Kanno, Yosuke, et al.; Plasminogen deficiency is associated with improved glucose tolerance, and lower DPP-4 activity; Diabetes Research and Clinical Practice 120, 2016; pp. 190-193.

Zhang, S.X., et al. Therapeutic potential of angiostatin in diabetic nephropathy, J. Am. Soc. Nephrol., vol. 17, pp. 475-586, 2006.

Lingohr et al., Specific Regulation of IRS-2 Expression by Glucose in Rat Primary Pancreatic Islet β-Cells, The Journal of Biological Chemistry, vol. 281, No. 23, pp. 15884-15892, Jun. 9, 2006.

First Office Action issued in corresponding Chinese Application No. 20168073671.8; dated Apr. 2, 2021; 17 pgs.

Office Action issued in corresponding European Application No. 16874924.0; dated Feb. 16, 2021; 9 pgs.

Office Action issued in corresponding European Application No. 16874928.1; dated Feb. 16, 2021; 9 pgs.

Office Action issued in corresponding Taiwan Application No. 106120493; dated Feb. 3, 2021; 9 pgs.

SUN, Yue-e et al., "Advancement on thrombolytic characteristic, function and clinical application of different fibrinolytic enzymes", China Journal of Chinese Materia Medica, vol. 35, No. 6, Mar. 2010, pp. 794-798.

Aisina, R. B. et al., "Structure and Function of Plasminogen/Plasmin System", Russian Journal of Bioorganic Chemistry, vol. 40, No. 6, Nov. 1, 2014, pp. 590-605 (642-657).

Xu, Ling et al., "Diabetic angiopathy and angiogenic defects", Fibrogenesis & Tissue Repair, vol. 5, No. 1, Aug. 1, 2012, pp. 13.

\* cited by examiner

METHOD FOR PREVENTING AND TREATING ANGIOCARDIOPATHY

RELATED APPLICATIONS

The present application is a National Phase of International Application Number PCT/CN2016/110453, filed Dec. 16, 2016, and claims the priority of International Application No. PCT/CN2015/097947, filed Dec. 18, 2015.

TECHNICAL FIELD

The present invention relates to the effect of plasminogen in the treatment and/or elimination of angiocardiopathy, especially angiocardiopathy caused by diabetes mellitus, thereby providing a new strategy for treating angiocardiopathy, especially angiocardiopathy and its related disorders caused by diabetes mellitus.

BACKGROUND ART

"Angiocardiopathy" refers to a disease of the histological and functional changes of the cardiovascular system, the main manifestations of which are typically cardiac changes caused by lesions of large vessels and microvessels. What can be seen clinically are electrocardiographic abnormalities, cardiac enlargement, arrhythmia, angina pectoris, painless myocardial infarction and heart failure. At present, diabetes mellitus has been a high-risk factor and predictor of angiocardiopathy, and the short-term or long-term prognosis of angiocardiopathy patients with diabetes mellitus is significantly worse than that of patients without diabetes mellitus.

"Diabetes mellitus" is a group of endocrine and metabolic syndromes of disordered metabolisms of carbohydrates, proteins, fats, water and electrolytes in the body caused by reduced insulin secretion or defects in insulin function resulting from combined action of a variety of genetic and environmental factors. It is characterized by chronic increase in blood glucose level, and can lead to chronic complications of multiple organ systems after a long illness, in which angiocardiopathy is a major complication of diabetes mellitus.

"Diabetic angiocardiopathy" refers to a disease with the histological and functional changes of the cardiovascular system caused by diabetes mellitus, and is one of the most common complications of diabetes mellitus. Diabetic angiocardiopathy as a complication of diabetes mellitus is a major hazard that is mainly manifested as cardiac changes caused by lesions of large vessels and microvessels typically. What can be seen clinically are electrocardiographic abnormalities, cardiac enlargement, arrhythmia, angina pectoris, painless myocardial infarction and heart failure. According to statistics, about 70%-80% of diabetics eventually die of cardiovascular complications. The incidences of atherosclerosis, hypertension, acute myocardial infarction, chronic heart failure and sudden death are increased significantly in diabetics. At present, diabetes mellitus has been a high-risk factor and predictor of angiocardiopathy, and the short-term or long-term prognosis of angiocardiopathy patients with diabetes mellitus is significantly worse than that of patients without diabetes mellitus.

Plasmin is a key component of the plasminogen activation system (PA system). It is a broad-spectrum protease that can hydrolyze several components of the extracellular matrix (ECM), including fibrin, gelatin, fibronectin, laminin, and proteoglycan[1]. In addition, plasmin can activate some pro-matrix metalloproteinases (pro-MMPs) to form active matrix metalloproteinases (MMPs). Therefore, plasmin is considered to be an important upstream regulator of extracellular proteolysis[2,3]. Plasmin is formed by the proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. There are uPA-specific cell surface receptors (uPARs) that have direct hydrolytic activity on certain cell surfaces[4,5].

Plasminogen (plg) is a single-stranded glycoprotein composed of 791 amino acids and has a molecular weight of about 92 kD[6,7]. Plasminogen is mainly synthesized in the liver and is abundantly present in the extracellular fluid. The content of plasminogen in plasma is about 2 µM. Therefore, plasminogen is a huge potential source of proteolytic activity in tissues and body fluids[8,9]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease[10]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered 38 kD fragment of plasminoge, comprising kringles 1-4, is a potent inhibitor of angiogenesis. This fragment is named as angiostatin and can be produced by the proteolysis of plasminogen via several proteases.

The main substrate of plasmin is fibrin, and the dissolution of fibrin is the key to prevent pathological thrombosis [11]. Plasmin also has substrate specificity for several components of ECM, including laminin, fibronectin, proteoglycan and gelatin, indicating that plasmin also plays an important role in ECM remodeling[7,12,13]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis[14]. In addition, plasmin has the ability to activate certain potential forms of growth factors[15-17]. In vitro, plasmin can also hydrolyze components of the complement system and release chemotactic complement fragments.

At present, methods for treating cardiovascular complications of diabetes mellitus mainly include controlling blood glucose, lowering blood lipids, controlling blood pressure and the like.

Our study surprisingly found that plasminogen can significantly repair the injury of the heart and blood vessel walls caused by diabetes mellitus, promote the dissolution of microthrombus, repair the injury of internal organs such as kidney, liver and retina tissue caused by diabetes mellitus, and recover the response function of injured nerves, thereby opening up a new therapeutic approach for diabetic complications such as diabetic angiocardiopathy.

DETAILED DESCRIPTION OF EMBODIMENTS

In one aspect, the present invention relates to a method of preventing and/or treating angiopathy in a subject, especially diabetic angiopathy, comprising administering an effective amount of plasminogen or plasmin to the subject. In one aspect, the present invention relates to the use of plasminogen or plasmin for preventing and/or treating angiopathy in a subject, especially diabetic angiopathy, comprising administering an effective amount of plasminogen or plasmin to the subject.

In one embodiment, the angiopathy is diabetic angiopathy, especially diabetic macroangiopathy, a small vessel disease, and/or diabetic microangiopathy. In one embodiment, the angiopathy comprises atherosclerosis, including atherosclerosis of the aortae and internal organs, especially atherosclerosis caused by diabetes mellitus, including atherosclerosis of the aortae and internal organs. In one embodiment, the diabetic microangiopathy includes altered microcirculatory function, vessel wall injury, microthrombosis, and/or microvascular occlusion. The present invention also relates to a method of preventing and/or treating angiocardiopathy, especially diabetic angiocardiopathy, in a subject comprising administering an effective amount of plasminogen or plasmin to a subject. In one embodiment, the angiocardiopathy include diabetic angiocardiopathy, cardiac hypertrophy, cardiac insufficiency, arrhythmia, angina pectoris, painless myocardial infarction and heart failure. In one embodiment, the diabetic angiocardiopathy is caused by diabetes mellitus-induced angiopathy of large vessels, small vessels, and microvessels.

In the above embodiment, the subject is a mammal, preferably human.

In one embodiment, the subject has a low level of plasmin or plasminogen. Specifically, the low level is innate, secondary and/or local.

In one embodiment, the angiocardiopathy of the present invention includes, but is not limited to, diabetic angiocardiopathy, hyperlipidemia, atherosclerosis, hypertension, coronary heart disease, angina pectoris, myocardial infarction, coronary insufficiency, chest tightness, palpitation, fluster and shortness of breath, arrhythmia, heart failure, etc.

In one embodiment, the plasminoge has at least 80%, 85%, 90%, 95%, 96%, 97%, 98% or 99% sequence identity with SEQ ID No.2, 6, 8, 10 or 12, and still has the activity of plasminoge. In one embodiment, the plasminoge is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminoge. In one embodiment, the plasminogen is a protein that comprises a plasminogen active fragment and still has the activity of plasminoge. In one embodiment, the plasminogen is selected from Glu-plasminoge, Lys-plasminoge, mini-plasminoge, micro-plasminoge, δ-plasminoge or any combination thereof. In one embodiment, the plasminogen is a conservatively substituted variant selected from Glu-plasminoge, Lys-plasminoge, mini-plasminoge, δ-plasminoge or micro-plasminoge. In one embodiment, the plasminoge is a human natural plasminoge, such as an ortholog of plasminogen shown in SEQ ID No.2, e.g., an ortholog of plasminoge from primates or rodents, for example, an ortholog of plasminoge from gorillas, rhesus monkeys, murine, cows, horses and dogs. Most preferably, the amino acid sequence of the plasminoge of the present invention is as shown in SEQ ID No.2, 6, 8, 10 or 12.

In one embodiment, the plasminogen is administered by systemic or topical route for treatment, preferably by the following routes: intravenous, intramuscular, subcutaneous and inhalation administration.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

The plasminogen may be administered alone or in combination with other drugs including but not limited to: cardiovascular drugs, anti-diabetic drugs, anti-thrombotic drugs, anti-infective drugs, anti-arrhythmic drugs, hypolipidemic drugs, etc.

In another aspect, the present invention relates to the use of plasminogen or plasmin in the manufacture of a medicament for preventing and/or treating angiopathy, especially diabetic angiopathy in a subject. In one aspect, the present invention relates to a method for manufacturing a medicament, comprising preparing a medicament for preventing and/or treating angiopathy, especially diabetic angiopathy in a subject using plasminogen or plasmin together with a pharmaceutically acceptable carrier.

In one embodiment, the angiopathy is diabetic angiopathy, especially diabetic macroangiopathy, a small vessel disease, and/or diabetic microangiopathy. In one embodiment, the angiopathy comprises atherosclerosis, especially atherosclerosis caused by diabetes mellitus, including atherosclerosis of the aortae and internal organs. In one embodiment, the diabetic microangiopathy includes altered microcirculatory function, vessel wall injury, microthrombosis, and/or microvascular occlusion.

The present invention also relates to the use of plasminogen or plasmin for preventing and/or treating angiocardiopathy, especially diabetic angiocardiopathy in a subject. In one embodiment, the angiocardiopathy include diabetic angiocardiopathy, cardiac hypertrophy, cardiac insufficiency, arrhythmia, angina pectoris, painless myocardial infarction and heart failure. In one embodiment, the diabetic angiocardiopathy is caused by diabetes mellitus-induced angiopathy of large vessels, small vessels, and microvessels.

In the above technical solutions, the subject is a mammal, preferably human.

In one embodiment, the subject has a low level of plasmin or plasminogen. Specifically, the low level is innate, secondary and/or local.

In one embodiment, the above-mentioned angiocardiopathy include, but is not limited to: diabetic angiocardiopathy, hyperlipidemia, atherosclerosis, hypertension, coronary heart disease, angina pectoris, myocardial infarction, coronary insufficiency, chest tightness, palpitation, fluster and shortness of breath, arrhythmia, heart failure, etc.

In one embodiment, the plasminogen is administered by systemic or topical route, preferably by the following routes: intravenous, intramuscular, subcutaneous and inhalation administration for treatment. In one embodiment, the plasminogen is administered by systemic or topical route for treatment, preferably by the following routes: intravenous, intramuscular, subcutaneous and inhalation administration.

The above plasminogen may be administered alone or in combination with other drugs including but not limited to: cardiovascular drugs, anti-diabetic drugs, anti-thrombotic drugs, anti-infective drugs, anti-arrhythmic drugs, hypolipidemic drugs, etc.

In one embodiment, the subject has a low level of plasmin or plasminogen. Specifically, the low level is innate, secondary and/or local.

In another aspect, the present invention relates to plasminogen or plasmin for preventing and/or treating angiopathy, especially diabetic angiopathy in a subject, and a pharmaceutical composition which comprises plasminogen or plasmin and is useful in the prevention and/or treatment of angiopathy, especially diabetic angiopathy in a subject. In one embodiment, the angiopathy, especially diabetic angiopathy, is diabetic macroangiopathy, a small vessel disease and/or diabetic microangiopathy. In one embodiment, the angiopathy includes atherosclerosis, especially diabetic atherosclerosis, including atherosclerosis of the aortae and internal organs. In one embodiment, the diabetic microangiopathy includes altered microcirculatory function, vessel wall injury, microthrombosis, and/or microvascular occlusion. The present invention also relates to plasminogen or plasmin for preventing and/or treating angiocardiopathy, especially diabetic angiocardiopathy in a subject, and a pharmaceutical composition which comprises plasminogen or plasmin and is useful in the prevention and/or treatment of angiocardiopathy, especially diabetic angiocardiopathy in a subject. In one embodiment, the angiocardiopathy include diabetic cardiopathy, comprising cardiac hypertrophy, cardiac insufficiency, arrhythmia, angina pectoris, painless myocardial infarction and heart failure. In one embodiment, the diabetic angiocardiopathy is caused by diabetes mellitus-induced angiopathy of large vessels, small vessels, and microvessels.

In one embodiment, the above-mentioned angiocardiopathy, especially angiocardiopathy caused by diabetes mellitus, includes but is not limited to: hyperlipidemia, atherosclerosis, hypertension, coronary heart disease, angina pectoris, myocardial infarction, coronary insufficiency, chest tightness, palpitation, fluster and shortness of breath, arrhythmia, heart failure, etc.

In one embodiment, the plasminoge has at least 80%, 85%, 90%, 95%, 96%, 97%, 98% or 99% sequence identity with SEQ ID No.2, 6, 8, 10 or 12, and still has the activity of plasminoge. In one embodiment, the plasminoge is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminoge. In one embodiment, the plasminogen is a protein that comprises a plasminogen active fragment and still has the activity of plasminoge. In one embodiment, the plasminogen is selected from Glu-plasminoge, Lys-plasminoge, mini-plasminoge, micro-plasminoge, δ-plasminoge or any combination thereof. In one embodiment, the plasminogen is a conservatively substituted variant selected from Glu-plasminoge, Lys-plasminoge, mini-plasminoge, δ-plasminogen or micro-plasminoge. In one embodiment, the plasminoge is a human natural plasminoge, such as an ortholog of plasminogen shown in SEQ ID No.2, e.g., an ortholog of plasminoge from primates or rodents, for example, an ortholog of plasminoge from gorillas, rhesus monkeys, murine, cows, horses and dogs. Most preferably, the amino acid sequence of the plasminoge of the present invention is as shown in SEQ ID No.2, 6, 8, 10 or 12.

In one embodiment, the plasminogen is administered by systemic or topical route, preferably by the following routes: intravenous, intramuscular, subcutaneous and inhalation administration for treatment.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In one embodiment, the subject has a low level of plasmin or plasminogen. Specifically, the low level is innate, secondary and/or local.

In another aspect, the present invention relates to an article or kit which comprises plasminogen or plasmin and is useful in the prevention and/or treatment of angiopathy, especially diabetic angiopathy in a subject. In one embodiment, the angiopathy, especially diabetic angiopathy, is diabetic macroangiopathy, a small vessel disease and/or diabetic microangiopathy. In one embodiment, the angiopathy comprises atherosclerosis, especially atherosclerosis caused by diabetes mellitus, including atherosclerosis of the aortae and internal organs. In one embodiment, the diabetic microangiopathy includes altered microcirculatory function, vessel wall injury, microthrombosis, and/or microvascular occlusion. The present invention also relates to an article or kit which comprises plasminogen or plasmin and is useful in the prevention and/or treatment of angiocardiopathy, especially diabetic angiocardiopathy in a subject. In one embodiment, the angiocardiopathy include diabetic angiocardiopathy, cardiac hypertrophy, cardiac insufficiency, arrhythmia, angina pectoris, painless myocardial infarction and heart failure. In one embodiment, the diabetic angiocardiopathy is caused by diabetes mellitus-induced angiopathy of large vessels, small vessels, and microvessels. In one embodiment, the article or kit comprises a container containing an effective dosage of plasminogen/plasmin. Preferably, the article or kit also comprises a container containing one or more other drugs. The article or kit can also contain instructions for use, which indicate that the plasminogen can be used to treat the angiopathy, especially diabetic angiopathy or diabetic angiocardiopathy, and can further indicate that the plasminogen can be administered before, simultaneously with, and/or after administration of other drugs. In one embodiment, the other drugs may include but are not limited to: cardiovascular drugs, anti-diabetic drugs, anti-thrombotic drugs, anti-infective drugs, anti-arrhythmic drugs, hypolipidemic drugs, etc. In one embodiment, the above-mentioned angiocardiopathy include, but is not limited to: diabetic angiocardiopathy, hyperlipidemia, atherosclerosis, hypertension, coronary heart disease, angina pectoris, myocardial infarction, coronary insufficiency, chest tightness, palpitation, fluster and shortness of breath, arrhythmia, and heart failure.

In one embodiment, the plasminoge has at least 80%, 85%, 90%, 95%, 96%, 97%, 98% or 99% sequence identity with SEQ ID No.2, 6, 8, 10 or 12, and still has the activity of plasminoge. In one embodiment, the plasminoge is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminoge. In one embodiment, the plasminogen is a protein that comprises a plasminogen active fragment and still has the activity of plasminoge. In one embodiment, the plasminogen is selected from Glu-plasminoge, Lys-plasminoge, mini-plasminoge, micro-plasminoge, 6-plasminogen or any combination thereof. In one embodiment, the plasminogen is a conservatively substituted variant selected from Glu-plasminoge, Lys-plasminoge, mini-plasminoge, 6-plasminogen or micro-plasminoge. In one embodiment, the plasminoge is a human natural plasminoge, such as an ortholog of plasminogen shown in SEQ ID No.2, e.g., an ortholog of plasminoge from primates or rodents, for example, an ortholog of plasminoge from gorillas, rhesus monkeys, murine, cows, horses and dogs. Most preferably, the amino acid sequence of the plasminoge of the present invention is as shown in SEQ ID No.2, 6, 8, 10 or 12.

In one embodiment, the plasminogen is administered by systemic or topical route, preferably by the following routes: intravenous, intramuscular, subcutaneous and inhalation administration for treatment.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In one embodiment, the subject has a low level of plasmin or plasminogen. Specifically, the low level is innate, secondary and/or local.

In one aspect, the present invention relates to the use of plasminogen or plasmin in the manufacture of a medicament, article and kit for preventing and/or treating angiopathy, especially injury (damage) to body tissues and internal organs caused by angiopathy in a subject. In one embodiment, the injury (damage) to tissues and internal organs includes injury (damage) to the brain, heart, liver, lungs, kidneys, nerves, retina, skin and gastrointestinal tract. In one aspect, the present invention relates to the use of plasminogen in the manufacture of a medicament, article or kit for preventing and/or treating a diabetic complication in a subject. In one embodiment, the diabetic complication is diabetic encephalopathy, diabetic cardiopathy, diabetic hepatopathy, diabetic nephropathy, diabetic pneumonopathy, diabetic neuropathy, diabetic angiopathy, diabetic retinopathy or diabetic dermopathy induced by diabetes mellitus.

In one aspect, the present invention relates to a method for manufacturing a medicament, comprising preparing a medicament, article or kit for preventing and/or treating angiopathy, especially the injury (damage) to body tissues and internal organs caused by angiopathy in a subject using plasminogen or plasmin and a pharmaceutically acceptable carrier. In one embodiment, the injury (damage) to tissues and internal organs includes injury (damage) to the brain, heart, liver, lungs, kidneys, nerves, retina, skin and gastrointestinal tract. In one aspect, the present invention relates to a method for manufacturing a medicament, comprising preparing a medicament, article or kit for preventing and/or treating a diabetic complication in a subject using plasminogen or plasmin and a pharmaceutically acceptable carrier. In one embodiment, the diabetic complication is diabetic encephalopathy, diabetic cardiopathy, diabetic hepatopathy, diabetic nephropathy, diabetic pneumonopathy, diabetic neuropathy, diabetic angiopathy, diabetic retinopathy or diabetic dermopathy induced by diabetes mellitus.

In one aspect, the present invention relates to plasminogen or plasmin, and a pharmaceutical composition, article or kit comprising the plasminogen or plasmin, which are useful in the prevention and/or treatment of angiopathy, especially the injury (damage) to body tissues and internal organs caused by angiopathy in a subject. In one embodiment, the injury (damage) to tissues and internal organs includes injury (damage) to the brain, heart, liver, kidneys, lungs, nerves, retina, gastrointestinal tract and skin. In one aspect, the present invention relates to plasminogen, and a pharmaceutical composition, article or kit comprising the plasminogen, which are useful in the prevention and/or treatment of a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic angiopathy, diabetic retinopathy or diabetic dermopathy induced by diabetes mellitus.

In one aspect, the present invention relates to a method for preventing and/or treating angiopathy, especially the injury (damage) to body tissues and internal organs caused by angiopathy in a subject, comprising administering plasminogen or plasmin or a pharmaceutical composition, article or kit comprising the plasminogen or plasmin to the subject. The present invention also relates to the use of plasminogen or plasmin, or a pharmaceutical composition, article or kit comprising the plasminogen or plasmin for preventing and/or treating angiopathy, especially the injury (damage) to body tissues and internal organs caused by angiopathy in a subject. In one embodiment, the injury (damage) to tissues and internal organs includes injury (damage) to the brain, heart, liver, lungs, kidneys, nerves, retina, gastrointestinal tract and skin. In one aspect, the present invention relates to a method for preventing and/or treating a diabetic complication in a subject, comprising administering plasminogen or plasmin, or a pharmaceutical composition, article or kit comprising the plasminogen or plasmin to the subject. The present invention also includes the use of plasminogen or plasmin, or a pharmaceutical composition, article or kit comprising the plasminogen or plasmin for preventing and/or treating a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic angiopathy, diabetic retinopathy or diabetic dermopathy induced by diabetes mellitus.

In one embodiment, the subject has a low level of plasmin or plasminogen. Specifically, the low level is innate, secondary and/or local.

In one embodiment, the plasminoge has at least 80%, 85%, 90%, 95%, 96%, 97%, 98% or 99% sequence identity with SEQ ID No.2, 6, 8, 10 or 12, and still has the activity of plasminoge. In one embodiment, the plasminoge is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminoge. In one embodiment, the plasminogen is a protein that comprises a plasminogen active fragment and still has the activity of plasminoge. In one embodiment, the plasminogen is selected from Glu-plasminoge, Lys-plasminoge, mini-plasminoge, micro-plasminoge, δ-plasminogen or any combination thereof. In one embodiment, the plasminogen is a conservatively substituted variant selected from Glu-plasminoge, Lys-plasminoge, mini-plasminoge, δ-plasminogen or micro-plasminoge. In one embodiment, the plasminoge is a human natural plasminoge, such as an ortholog of plasminogen shown in SEQ ID No.2, e.g., an ortholog of plasminoge from primates or rodents, for example, an ortholog of plasminoge from gorillas, rhesus monkeys, murine, cows, horses and dogs. Most preferably, the amino acid sequence of the plasminoge of the present invention is as shown in SEQ ID No.2, 6, 8, 10 or 12.

In one embodiment, the plasminoge is administered by systemic or topical route, preferably by the following routes: topical, intravenous, intramuscular, subcutaneous, inhalation, intraspinal, local injection, intraarticular injection or rectal route. In one embodiment, the topical administration is performed by applying a dressing and/or a catheter containing plasminoge in the area of the thrombus.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

The above plasminoge may be administered alone or in combination with other drugs, for example, drugs for treating angiocardiopathy, drugs for treating arrhythmia, drugs for treating diabetes mellitus and the like, to treat other diseases accompanying with pathological thrombosis.

In one embodiment, the subject has a low level of plasmin or plasminogen. Specifically, the low level is innate, secondary and/or local.

The present invention explicitly encompasses all the combinations of technical features belonging to the embodiments of the present invention, and these combined technical solutions have been explicitly disclosed in the present application, as if the above technical solutions were individually and explicitly disclosed. In addition, the present invention also explicitly encompasses all the subcombinations of the various embodiments and elements thereof, and these subcombinations have been disclosed herein, as if each of such subcombinations was individually and explicitly disclosed herein.

DETAILED DESCRIPTION OF EMBODIMENTS

"Angiocardiopathy" refers to a disease of the histological and functional changes of the cardiovascular system, the main manifestations of which are typically cardiac changes caused by lesions of large vessels and microvessels. What can be seen clinically are electrocardiographic abnormalities, cardiac enlargement, arrhythmia, angina pectoris, painless myocardial infarction and heart failure.

"Diabetes mellitus" is a series of dysmetabolic syndromes of carbohydrates, proteins, fats, water, electrolytes and the like that are caused by islet hypofunction, insulin resistance and the like resulting from the effects of genetic factors, immune dysfunction, microbial infections and toxins thereof, free radical toxins, mental factors and other various pathogenic factors on the body, and is mainly characterized by hyperglycemia clinically.

"Diabetic complications" are damages to or dysfunctions of other organs or tissues of the body caused by poor blood glucose control during diabetes mellitus, including damages to or dysfunctions of the liver, kidneys, heart, retina, nervous system damage and the like. According to statistics of the World Health Organization, there are up to more than 100 diabetic complications, and diabetes mellitus is a disease currently known to have the most complications. These complications of diabetes mellitus are mainly due to the injuries of large vessels, small vessels, and microvessels in various organs of patients.

"Diabetic angiopathy" mainly refers to atherosclerosis of arteries of the aortae and various internal organs caused by diabetes mellitus, including atherosclerosis of the large and small arteries of the brain, lungs, heart, liver, spleen, and kidneys; as well as the corresponding resulting organ and tissue lesions. Its pathogenesis includes the following aspects: 1) persistent hyperglycemia increases blood viscosity and coagulation, which in turn causes arterial vascular elasticity to be weakened or even lost; 2) abnormal lipid metabolism promotes the accumulation of cholesterol and cholesterol esters in the cells, leading to the occurrence and development of atherosclerosis; 3) injury of arterial wall endothelial cells occurs because hemodynamic changes cause long-term mechanical impact of blood on the vascular endothelium, resulting in endothelial injury; as a result, platelets, fibrin, etc. adhere to and accumulate at the site of injury to form thrombi, which can further lead to inflammation; and 4) increased glycoprotein factors involved in the blood coagulation mechanism promote aggregation and adhesion of platelets and fibrin at the damaged subendothelial layer and decrease the dissolution capacity, thereby forming the thrombus. Therefore, when mentioned in the technical solutions of the claims in the present invention, the term "diabetic angiopathy" covers diabetes mellitus-induced atherosclerosis and thrombus, and the corresponding resulting organ and tissue lesions.

"Diabetic microangiopathy" refers to microangiopathy caused by varying degrees of abnormalities in the microcirculation of various body organs or tissues of diabetics. The process of microangiopathy formation roughly comprises microcirculation function changes; vascular wall injury occurs, such as endothelial injury, and basement membrane thickening; and blood viscosity increases, red blood cells aggregate, platelets adhere and accumulate, eventually leading to microthrombosis and/or microvascular occlusion.

The above-mentioned two types of "diabetic angiopathy" causes local vascular injury to tissues or organs, poor blood flow, hypoxia of cells, and formation of blood clots, thrombus and inflammation, and further affects the functions of peripheral tissues and organs, thereby causing diabetic complications.

"Diabetic angiocardiopathy" refers to a disease with the histological and functional changes of the cardiovascular system caused by diabetes mellitus, and is one of the most common diabetic complications and is mainly caused by diabetes mellitus-induced angiopathy of large vessels, small vessels, and microvessels. Among them, the patient's clinical manifestations may include electrocardiographic abnormalities, cardiac enlargement, arrhythmia, angina pectoris, painless myocardial infarction and heart failure. According to statistics, about 70%-80% of diabetics eventually die of cardiovascular complications. The incidences of atherosclerosis, hypertension, acute myocardial infarction, chronic heart failure and sudden death are increased significantly in diabetics. At present, diabetes mellitus has been a high-risk factor and predictor of angiocardiopathy, and the short-term or long-term prognosis of angiocardiopathy patients with diabetes mellitus is significantly worse than that of patients without diabetes mellitus.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No.4) of the natural human-derived plasminogen containing a signal peptide, is a glycoprotein composed of 810 amino acids, which has a molecular weight of about 92 kD and is synthesized mainly in the liver and capable of circulating in the blood; and the cDNA sequence encoding this amino acid sequence is as shown in SEQ ID No.3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No.1; and the amino acid sequence is as shown in SEQ ID No.2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain[18,19]. The amino acid sequence (SEQ ID No.8) of δ-plasminogen has been reported in the literature[19], and the cDNA sequence encoding this amino acid sequence is as shown in SEQ ID No.7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid)[20]; the amino acid sequence is as shown in SEQ ID No.10; and the cDNA sequence encoding this amino acid sequence is as shown in SEQ ID No.9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid)[21], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No.12; and the cDNA sequence encoding this amino acid sequence is as shown in SEQ ID No.11.

The "thrombus" is the product of the blood coagulation process. The blood coagulation process is the defense mechanism that the body maintains the integrity of the closed high pressure circulatory system. Under normal circumstances, the process should remain inactivated, but when the tissue is damaged, the mechanism needs to be activated immediately to reduce blood extravasation. When blood vessels are damaged, fibrinogen dissolved in plasma under the action of thrombin will eventually be converted into fibrin polymers that are insoluble in water and interlaced with each other to form a net, which will entrap blood cells, so that blood clots are formed and the blood coagulation process is completed. In this process, the size ratio of the blood clot to the wound is crucial. Therefore, there should be a balance between molecules that initiate the blood clot formation (fibrin, thrombin) and molecules that dissolve blood clots (plasmin, plasminogen activator, etc.). However, in the course of pathology, the disruption of this balance will result in excess blood clot forming molecules, which in turn form the thrombus, which is a "pathological thrombus".

In the human body, thrombi can occur at any location with blood flow and are currently divided into two major categories: venous thrombi and arterial thrombi. Venous thrombi result from blood clots produced in the veins. The most common types of venous thrombi are: deep venous thrombi (DVT), which usually affects limb veins such as the femoral vein, causing pain and redness in the affected area; portal venous thrombi, which can affect the hepatic portal veins, leading to pancreatitis, liver cirrhosis, diverticulitis, or cholangiocarcinoma; renal venous thrombi, leading to renal embolism; internal jugular venous thrombi, which can cause systemic septicemia, pulmonary embolism and other complications; and cerebral venous thrombi, leading to headaches, visual abnormalities, strokes and other symptoms in patients. Arterial thrombi may result in infarcts of almost any organ in the body, and induce disorders, including, but not limited to: cerebral infarction, myocardial infarction, thrombotic stroke, atherosclerotic disease, unstable angina pectoris, intractable angina pectoris, transient ischemic attack, pulmonary embolism, etc.

In the case of diabetes mellitus, injury of arterial wall endothelial cells occurs because hemodynamic changes cause long-term mechanical impact of blood on the vascular endothelium, resulting in endothelial injury; as a result, platelets, fibrin, etc. adhere to and accumulate at the site of injury to form thrombi. In the present invention, it was found that plasminogen can significantly increase the D-dimer in the serum of diabetic mice, and the local fibrin in the heart, liver, kidneys, and nerve tissues is significantly reduced compared to the control group, indicating that plasminogen can promote the dissolution of microthrombi in diabetic mice. The present invention encompasses the treatment of microthrombi in diabetes mellitus with plasminogen.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

Those skilled in the art can understand that all the technical solutions of the plasminogen of the present invention are suitable for plasmin Therefore, the technical solutions described in the present invention cover plasminogen and plasmin.

The thrombus of the present invention includes fresh thrombus and old thrombus. The terms "fresh thrombus" and "acute thrombus" of the present invention can be used interchangeably; and "old thrombus" and "chronic thrombus" can be used interchangeably.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID NO: 14, or an amino acid sequence having an amino acid sequence identity of at least 80%, 90%, 95%, 96%, 97%, 98% or 99% with SEQ ID NO: 14. Therefore, plasminogen of the present invention comprises a protein comprising the plasminogen active fragment and still having plasminogen activity.

At present, methods for determining plasminoge and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminoge activators in plasma, detection of inhibitor antigens of tissue plasminoge activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminoge activity using a spectrophotometer. In addition, plasminoge activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity and hydrophobicity). Amino acids with similar properties are well known. For example, arginine, histidine and lysine are hydrophilic basic amino acids and are interchangeable. Similarly, isoleucine is a hydrophobic amino acid that can be replaced by leucine, methionine or valine Therefore, the similarity of two proteins or amino acid sequences with similar functions may be different. For example, the similarity (identity) is 70%-99% based on the MEGALIGN algorithm "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowly method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues), and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fractionX/Y×100 wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of Enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (eg, mammalian cells cultured in in vitro cell culture) can also be used to express and produce the protein of the invention (eg, polynucleotides encoding the subject protein). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the plasminogen and the like.

Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or nonionic surfactants, such as TWEEN™, PLURONICS™ or polyethylene glycol (PEG).

The formulations of the invention may also comprise one or more active compounds required for the particular disorder to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and ethyl-L-glutamic acid (Sidman et al. Biopolymers 22:547 (1983)), nondegradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulthydryl residues, lyophilizing from acidic solutions, controlling moisture content, using appropriate additives, and developing specific polymer matrix compositions.

Administration and Dosage

The pharmaceutical composition of the present invention can be administered in different ways, for example by intravenous, intraperitoneal, subcutaneous, intracranial, intrathecal, intraarterial (e.g., via carotid), intramuscular, intranasal, topical or intradermal administration or spinal cord or brain delivery. An aerosol preparation, such as a nasal spray preparation, comprises purified aqueous or other solutions of the active agent along with a preservative and isotonic agent. Such preparations are adjusted to a pH and isotonic state compatible with the nasal mucosa.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, such about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety of diabetic angiocardiopathy and its related disorders are required to be assessed real-timely and regularly.

Treatment Efficacy and Treatment Safety

One embodiment of the present invention relates to the judgment of treatment efficacy and treatment safety after treating a subject with plasminogen. The method for judging the treatment efficacy includes, but is not limited to, measuring the blood pressure, electrocardiogram, blood routine, urine routine, blood lipids, blood glucose, and hemodynamics of the subject. Specifically, the following tests were performed on the subject: 1) cardiovascular ultrasound for comprehensive diagnosis, detection of the size of each of atria and ventricles, ventricular wall motion, blood flow velocity, and cardiac function; 2) detection of concentrations of myocardial markers, such as C-reactive protein (CRP), myoglobin (Mb), creatine kinase MB isoenzyme (CK-MB), B-type natriuretic peptide (BNP), and the like, which are important diagnostic markers for acute myocardial infarction. These measurements are expected to return to the normal range or be improved after the subject receives the plasminogen treatment of the present invention, for example, Mb in the male subjects returns to 19-92 µg/L, and that in the females returns to 12-76 µg/L; and 3) dynamic electrocardiogram monitoring. In addition, the present invention also relates to the judgment of the safety of the therapeutic regimen during and after treating a subject with plasminogen, and relates to the monitoring of various adverse events.

Articles or Kits

One embodiment of the present invention relates to an article or kit comprising plasminogen or plasmin of the present invention useful in the treatment of angiocardiopathy, especially angiocardiopathy and its related disorders caused by diabetes mellitus. The article preferably includes a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen/plasmin. The label on or attached to the container indicates that the composition is used to treat the angiocardiopathy of the present invention, especially angiocardiopathy and its related disorders caused by diabetes mellitus. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to a user of the composition to administer the plasminogen composition and other drugs to treat an accompanying disease to a patient.

EXAMPLES

Example 1. Effect of Plasminogen on Body Weight of Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. The mice were weighted on days 0, 4, 7, 11, 16, 21, 26 and 31.

Figure 1:
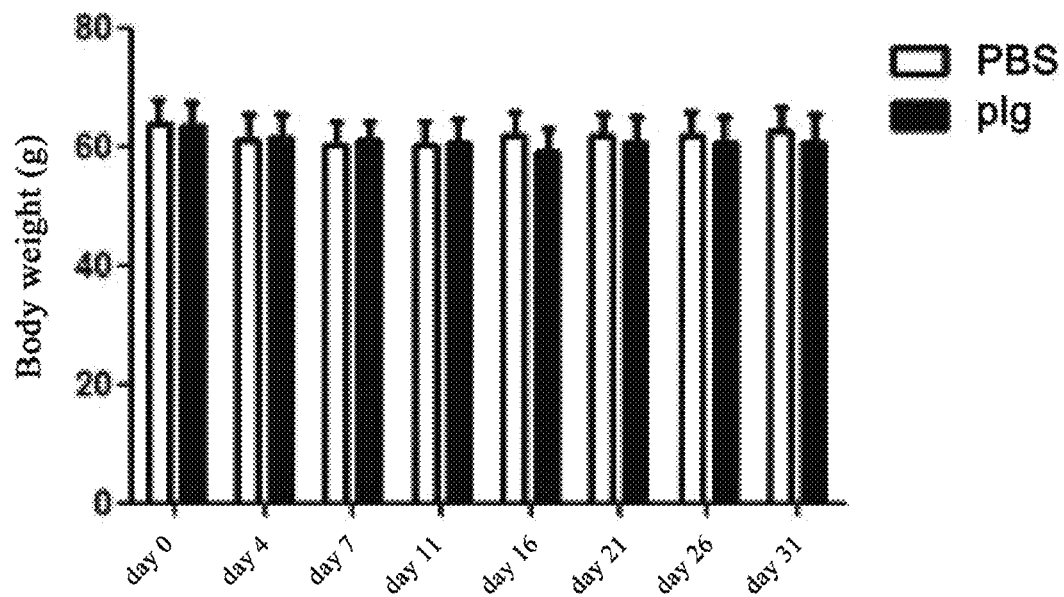
FIG. 1 shows changes in body weight after administration of plasminogen to 24-25-week-old db/db mice for 31 consecutive days. There was no significant difference in body weight on days 0, 4, 7, 11, 16, 21, 26 and 31 between the group administered with plasminogen and the control group administered with vehicle PBS.

The results showed that there was no significant difference in body weight on days 0, 4, 7, 11, 16, 21, 26 and 31 between the group administered with plasminogen and the control group administered with vehicle PBS (FIG. 1). It shows that plasminogen has little effect on the body weight of the animals, and the treatment by administering plasminogen has no significant effect on the body weight of the animals.

Example 2. Repair Effect of Plasminogen on Injury of the Mouse Myocardium

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the hearts were fixed in 10% neutral formalin fix solution for 24 hours. The fixed hearts were paraffin-embedded after dehydration with alcohol gradient and permeabilization with xylene. The thickness of the tissue sections was 5 µm. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient and observed under a microscope at 400×.

Figure 2:
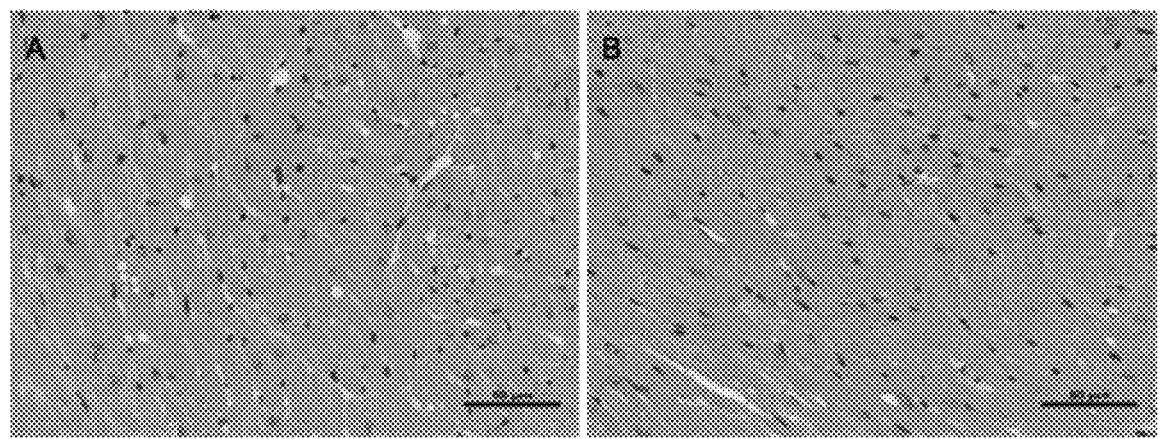
FIG. 2 shows the results of cardiac HE staining after administration of plasminogen to 24-25-week-old db/db mice for 31 consecutive days.

The results showed that in the control group administered with vehicle PBS, the cardiomyocyte hypertrophy occurred, the spindle-shaped hypertrophic nuclei can be incidentally seen, with mild steatosis, vacuolization shapes, mild inflammatory cell infiltration visible at the edge of the blood vessel or in the myocyte space, and the myofiber space was widened (FIG. 2A); in the group administered with plasminogen, the cardiomyocytes are in a round or spindle shape, with fewer hypertrophic cells than the control group, and denser myofibrillar space than the control group, and the inflammatory cell infiltration and steatosis were significantly reduced compared to the control group administered with vehicle PBS (FIG. 2B). It shows that the injection of plasminogen can significantly repair the injury of the mouse myocardium.

Example 3. Plasminogen Promotes Cardiac Fibrin Hydrolysis in Mice

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the hearts were fixed in 10% neutral formalin fix solution for 24 hours. The fixed heart tissues were paraffin-embedded after dehydration with alcohol gradient and permeabilization with xylene. The thickness of the tissue sections was 5 µm. The sections were dewaxed, rehydrated, washed with water once, incubated with 3% hydrogen peroxide for 15 minutes, and washed with water twice for 5 minutes each time. The sections were blocked with 10% normal goat serum solution (Vector laboratories, Inc., USA) for 1 hour; then the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Fibrinogen is the precursor of fibrin, and in the presence of tissue injury, as a stress response to the body's injury, fibrinogen is hydrolyzed into fibrin[22-24]. Therefore, fibrin levels can be used as a sign of the degree of injury. Fibrin is also the main component of thrombosis after tissue is injured. Therefore, fibrin levels can also be used as a marker of thrombi.

Figure 3:
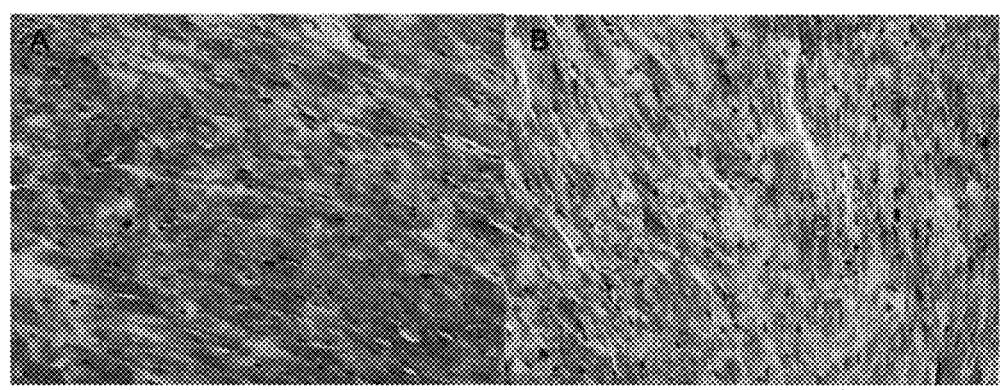
FIG. 3 shows the results of cardiac fibrinogen staining after administration of plasminogen to 24-25-week-old db/db mice for 31 consecutive days.

The results showed that the positive staining of fibrin in mouse heart tissue in the group administered with plasminogen (FIG. 3B) was lighter than that in the control group administered with vehicle PBS (FIG. 3A), indicating that fibrin deposition in heart tissues in the group administered with plasminogen was reduced, reflecting that plasminogen can promote the repair of the heart tissue injury, also indicating that plasminogen can promote the dissolution of thrombi in heart tissues.

Example 4. Repair Effect of Plasminogen on Injury of the Mouse Arterial Wall

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the aortic arches were fixed in 10% neutral formalin fix solution for 24 hours. The fixed hearts were paraffin-embedded after dehydration with alcohol gradient and permeabilization with xylene. The thickness of the tissue sections was 5 µm. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient and observed under a microscope at 400×.

Figure 4:
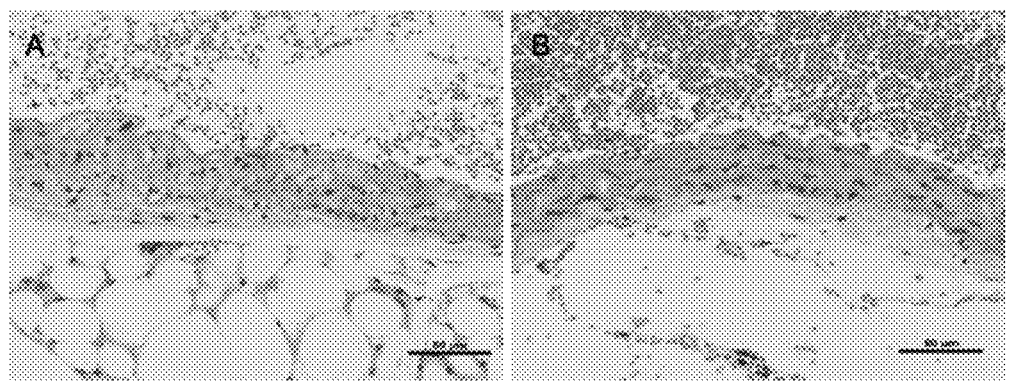
FIG. 4 shows the results of aortic arch HE staining after administration of plasminogen to 24-25-week-old db/db mice for 31 consecutive days.

The results showed that in the control group administered with vehicle PBS, there were foam cell depositing upon the vascular wall, the middle layer elastic membranes were arranged in disorder, the blood vessel walls were thickened, and the walls of the vessels were uneven in convex-concave forms (FIG. 4A); in the group administered with plasminogen, the middle layer elastic membrane structure is regular and wavy, and the thickness of the vascular wall is uniform (FIG. 4B). It shows that the injection of plasminogen has repair effect on aortic wall injury.

Example 5. Plasminogen Significantly Alleviates Myocardial Injury

Twenty-eight male db/db mice aged 24-25 weeks were randomly divided into two groups, twelve in the control group administered with vehicle PBS and sixteen in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On day 32, blood was taken from the removed eyeballs and centrifuged at 3500 r/min for 15-20 minutes, and the supernatant was used for the determination of cardiac troponin I concentration in serum.

Figure 5:
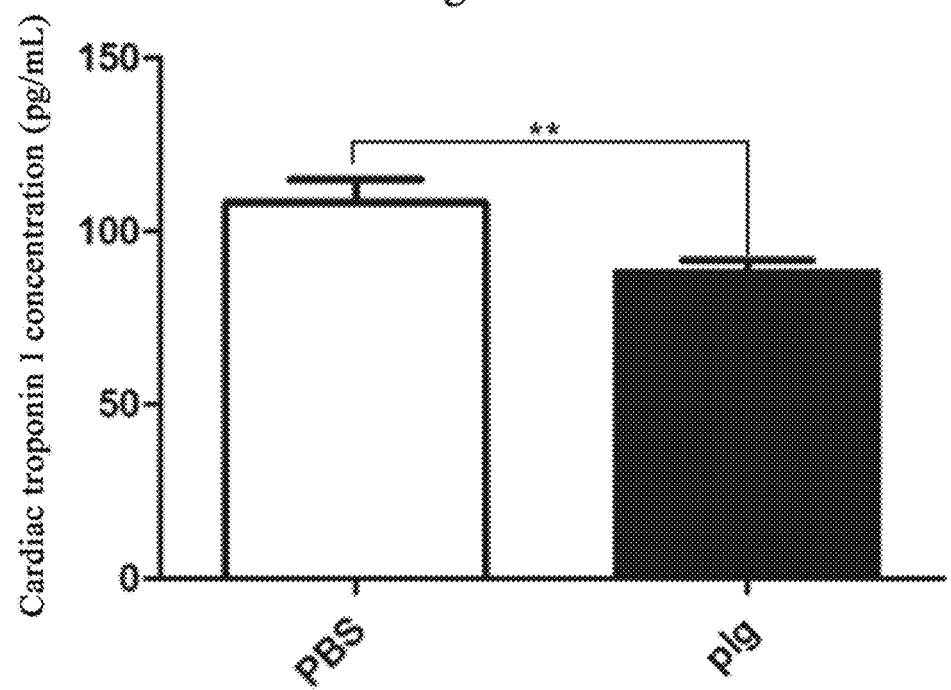
FIG. 5 shows the serum cardiac troponin concentration measurement results after administration of PBS or plasminogen to 24-25-week-old mice for 31 days.

Cardiac troponin I (CTNI) is an important marker of myocardial injury, and its serum concentration can reflect the extent of myocardial injury[25]. The results showed that the cardiac troponin I concentration in the group administered with plasminogen was significantly lower than that in the control group administered with vehicle PBS, and there was an extremely significant statistical difference (FIG. 5). It shows that plasminogen can significantly alleviates myocardial injury.

Example 6. Plasminogen Promotes Dissolution of Microthrombi

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. 24 hours after the last administration, blood was taken from the removed eyeballs, and the whole blood was left standing to obtain serum for detecting the D-dimer content in the blood.

Figure 6:
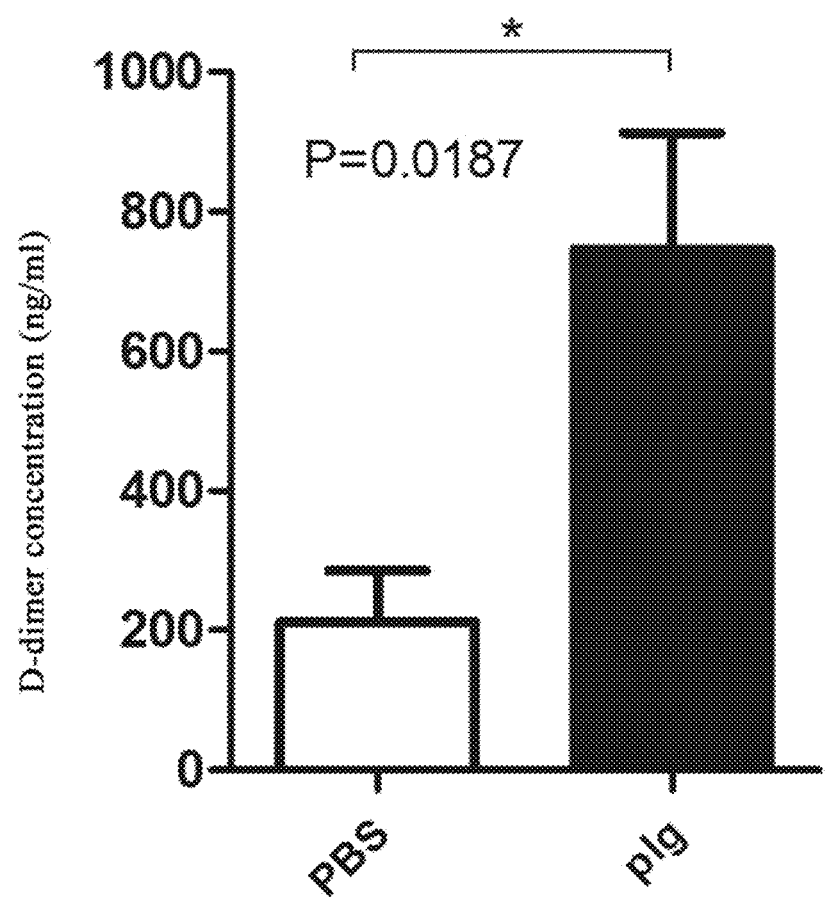
FIG. 6 shows the detection results of serum D-dimer content after administration of plasminogen to 24-25-week-old db/db mice for 15 consecutive days.

The results showed that after administration of plasminogen for 15 days, the content of D-dimer in the serum increased significantly (FIG. 6), indicating that plasminogen can significantly promote the dissolution of microthrombi.

Example 7. Plasminogen Promotes Repair of Retinal Capillary Injury in Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the left eyeballs were fixed in paraformaldehyde fix solution for 24 hours. The retina was detached from the fixed eyeballs and placed in a 1 mL EP tube containing 3% pancreatin (Solarbio), and shaken for digestion in a shaker at 37° C. for 2-3 h. After the retina was softened and detached, the retina was carefully transferred into an EP tube filled with distilled water and shaken in a shaker at 37° C. for 2-3 h to detach excess tissues from the retina. The retina was gently pipetted, leaving only the blood vessel layer, and then spread on a glass slide and air dried. The retina was stained in periodic acid-Schiff solution (PAS staining), differentiated with 1% hydrochloric acid in alcohol, and returned to blue with ammonia water. The sections were sealed after dehydration with alcohol gradient and permeabilization with xylene, and observed under a microscope at 400×.

Figure 7:
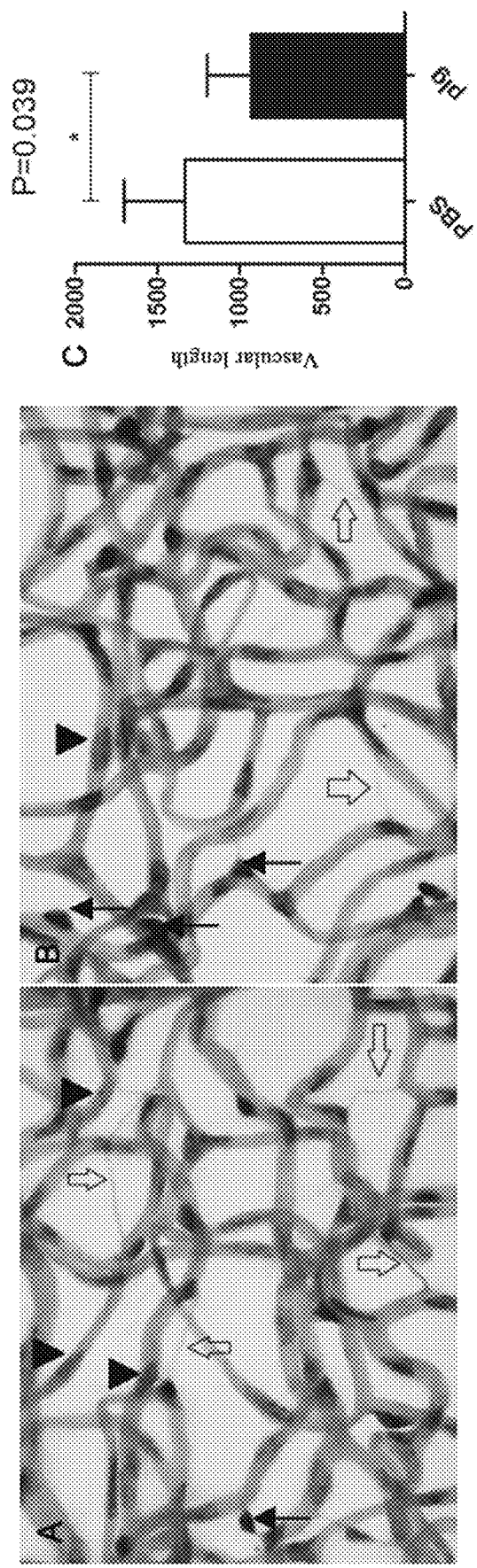
FIG. 7 shows the observed results of PAS staining of the retina after administration of plasminogen to 24-25-week-old db/db mice for 31 consecutive days.

From the experimental results, it can be seen that compared with the plasminogen group (FIG. 7B), the capillary diameters of the db/db mice in the control group administered with vehicle PBS (FIG. 7A) were different, in which the vascular walls were thickened and darkly stained, the vascular endothelial cells (Δ) were proliferated, and the pericytes (↓) were decreased remarkably; It was found from quantitative analysis that compared with mice in the control group administered with vehicle PBS, those in the group administered with plasminogen had significantly reduced cell-free vascular length (FIG. 7C), and the statistical analysis results showed a significant difference. It shows that plasminogen can significantly promote the repair of retinal capillary injury in mice, thus promoting the repair of retinal injury.

Example 8. Plasminogen Reduces Fibrin Deposition in the Kidneys of Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin[22-24]. Therefore, fibrin levels can be used as a sign of the degree of injury. Fibrin is also the main component of thrombosis after tissue is injured. Therefore, fibrin levels can also be used as a marker of thrombi.

Figure 8:
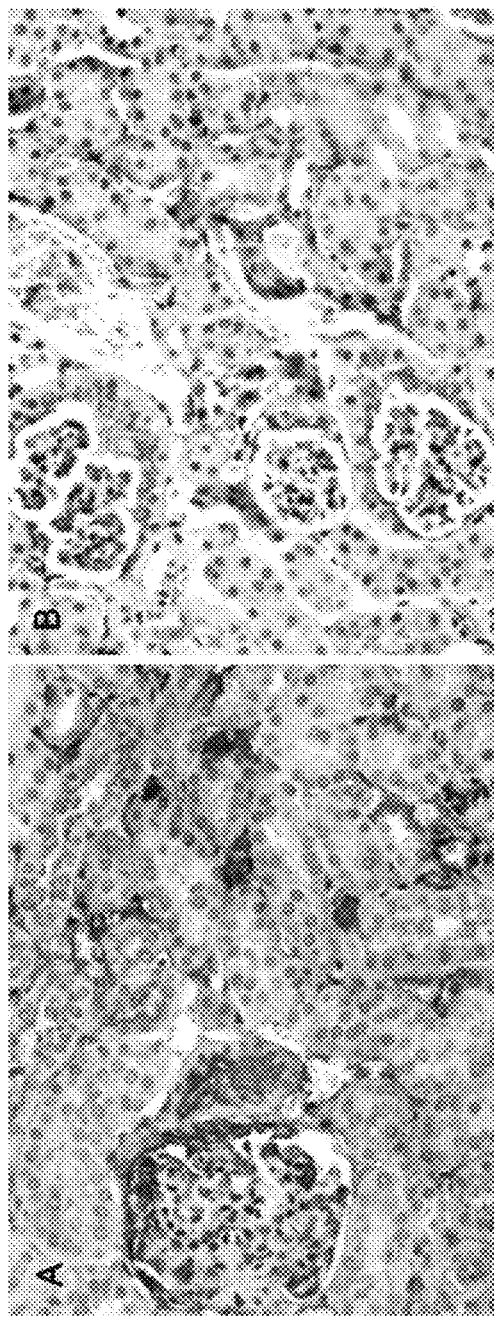
FIG. 8 shows the observed results of fibrin immunostaining of the kidneys after administration of plasminogen to 24-25-week-old db/db mice for 31 consecutive days.

The results showed the fibrinogen-positive staining in the group administered with plasminogen (FIG. 8B) was lighter than that in the control group administered with vehicle PBS (FIG. 8A). It shows that injection of plasminogen can significantly reduce fibrin deposition in the kidneys of mice, plasminogen has a significant repair effect on the kidney injury in mice, and it also shows that plasminogen can promote the dissolution of thrombi in kidney tissues.

Example 9. Plasminogen Promotes the Expression of Bcl-2, an Apoptosis Inhibitory Protein, in the Kidneys of Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse Bcl2 antibody (Abcam) at 4° C. overnight and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Figure 9:
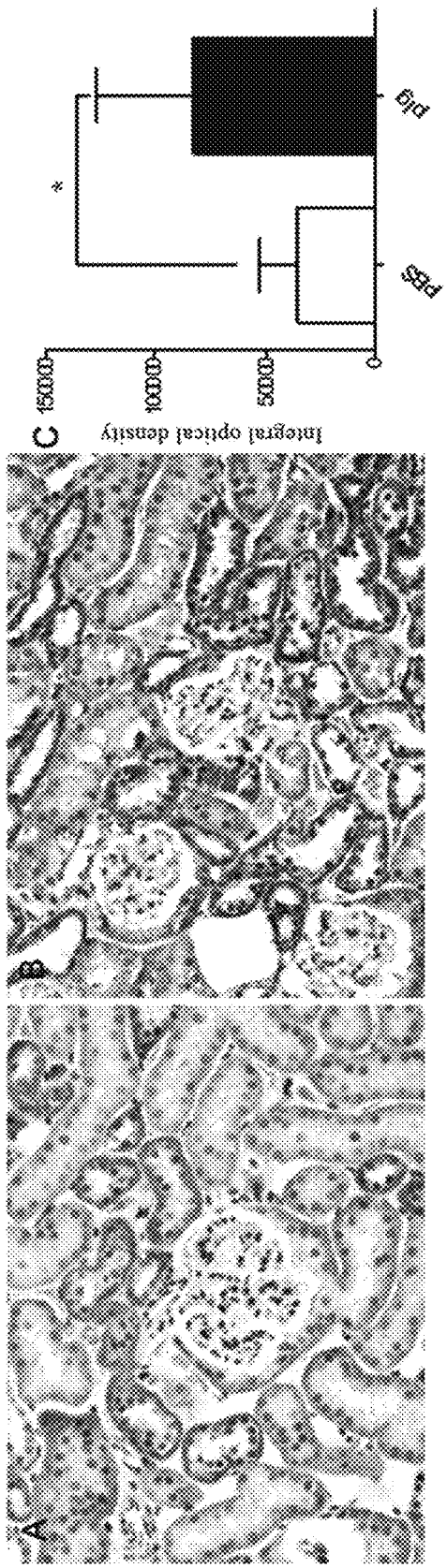
FIG. 9 shows the observed results of Bcl2 immunostaining of the kidneys after administration of plasminogen to 24-25-week-old db/db mice for 31 consecutive days.

Bcl-2 is an apoptosis inhibitory protein, and its expression will be down-regulated under the action of an apoptosis stimulating factor [26, 27]. The Bcl-2 immunohistochemical results showed that the positive expression staining of tubular epithelial cells in mice in the group administered with plasminogen (FIG. 9B) was significantly darker than that of tubular epithelial cells in those in the control group administered with vehicle PBS (FIG. 9A), and the former had a wider range of staining. The results of quantitative analysis were consistent with the observations, and there were significant differences (FIG. 9C). This indicated that plasminogen can promote the expression of Bcl-2, an apoptosis inhibitory molecule, in the kidneys of mice, and thus can inhibit the apoptosis in the kidney tissues of mice.

Example 10. Plasminogen Reduces the Fibrin Level in Liver Tissues

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and liver tissues were fixed in 10% neutral formalin fix solution for 24 hours. The fixed liver tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin[22,24]. Therefore, fibrin levels can be used as a sign of the degree of injury. Fibrin is also the main component of thrombosis after tissue is injured. Therefore, fibrin levels can also be used as a marker of thrombi.

Figure 10:
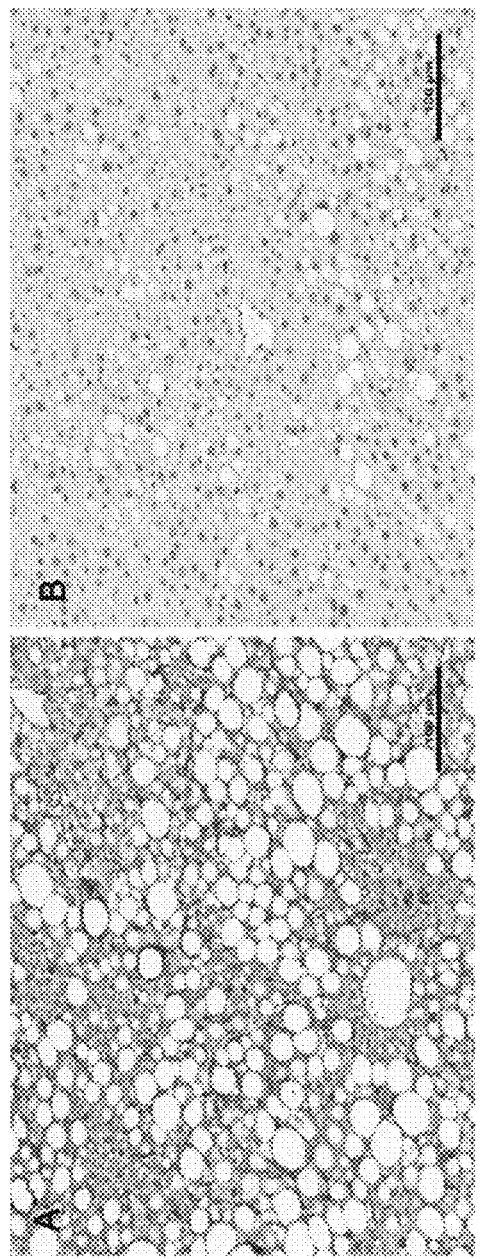
FIG. 10 shows the observed results of fibrin immunostaining of the liver after administration of plasminogen to 24-25-week-old db/db mice for 31 consecutive days.

The study found that compared with mice in the control group administered with vehicle PBS (FIG. 10A), those in the group administered with plasminogen (FIG. 10B) had a lighter fibrin-positive staining in the liver tissues, indicating that injection of plasminogen can significantly reduce fibrin deposited in the liver of mice, reflecting the significant repair effect of plasminogen on the liver injury of mice, and also indicating that plasminogen can promote the dissolution of thrombi in liver tissues.

Example 11. Plasminogen Promotes Repair of Inflammation in Liver Tissues

Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed 31 days after administration of plasminogen, and liver tissues were fixed in 10% neutral formalin fix solution for 24 hours. The fixed liver tissues were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were blocked with 10% normal goat serum (Vector laboratories, Inc., USA) for 1 hour, and after the time was up, the serum was thrown away, and the tissues were circled with a PAP pen. The sections were incubated with a rabbit polyclonal antibody against F4/80 (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Figure 11:
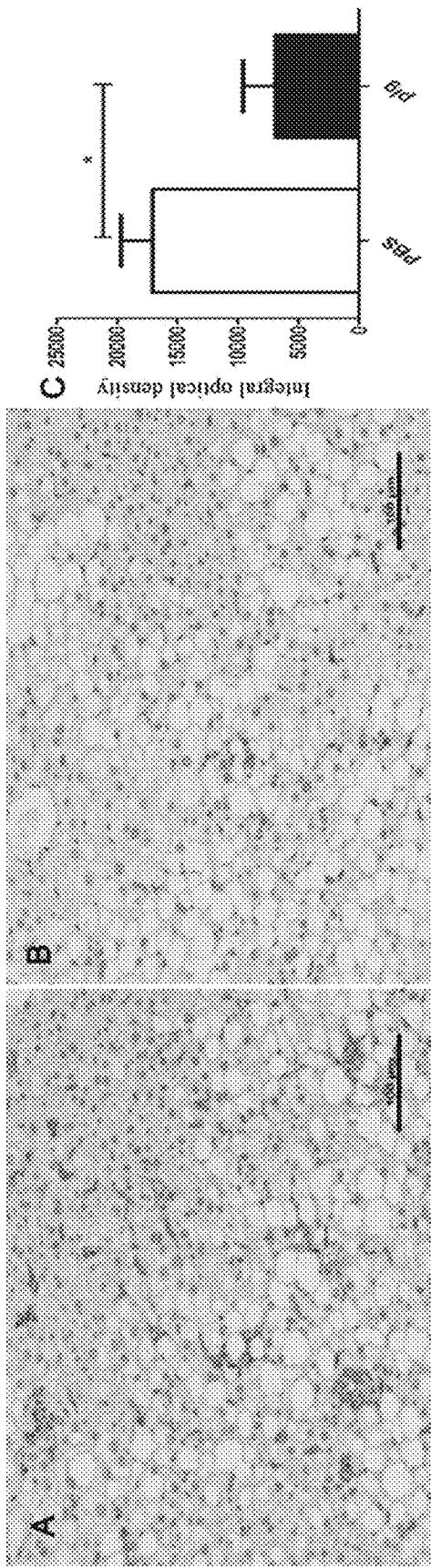
FIG. 11 shows the observed results of F4/80 immunostaining of the liver after administration of plasminogen to 24-25-week-old db/db mice for 31 consecutive days.

F4/80 is a macrophage marker. Macrophages, as the main phagocytic cells in the inflammatory phase, are responsible for the removal of necrotic debris of tissues and cells and pathogens at the body site of injury; therefore, the amount of local macrophages can indicate the degree and stage of an inflammatory response. The experimental results showed that compared with mice in the control group administered with vehicle PBS (FIG. 11A), the F4/80 positive level was significantly reduced in those in the group administered with plasminogen (FIG. 11B), indicating that inflammation of the liver tissues can be alleviated by administration of plasminogen. FIG. 11C shows the results of quantitative analysis of F4/80 immunohistochemical positive expression, in which the expression of F4/80 in mice in the group administered with plasminogen was significantly reduced with statistical difference, indicating that injection of plasminogen can significantly promote the repair of liver inflammation of mice.

Example 12. Plasminogen Promotes the Repair of the Ability of Mice with Nerve Injury to Respond to Mechanical Allodynia Ten male db/db mice aged 24-25 weeks were randomly divided into two groups, five in the control group administered with vehicle PBS and five in the group administered with plasminogen, respectively. The day when the experiment began was recorded on Day 0, the mice were weighed and grouped, and the physiological experiment was initiated. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration of plasminogen, animals were detected for their sensitivity to mechanical injury using Von-Frey filaments (Stoelting, USA). With 2.0 g force as the starting force, the left foot was first detected. If there were 2 paw withdrawals for 5 stimulations, it was positive; and if it was positive, the right foot was then stimulated with a smaller force. If it was negative, the right foot was stimulated with a larger force, the left and right feet were thus alternately stimulated for a total of 6 stimulations at a stimulation interval of 5 minutes, and then the 50% paw withdrawal threshold was calculated according to the method introduced in S. R. Chaplan et. al. (1994)[28].

Figure 12:
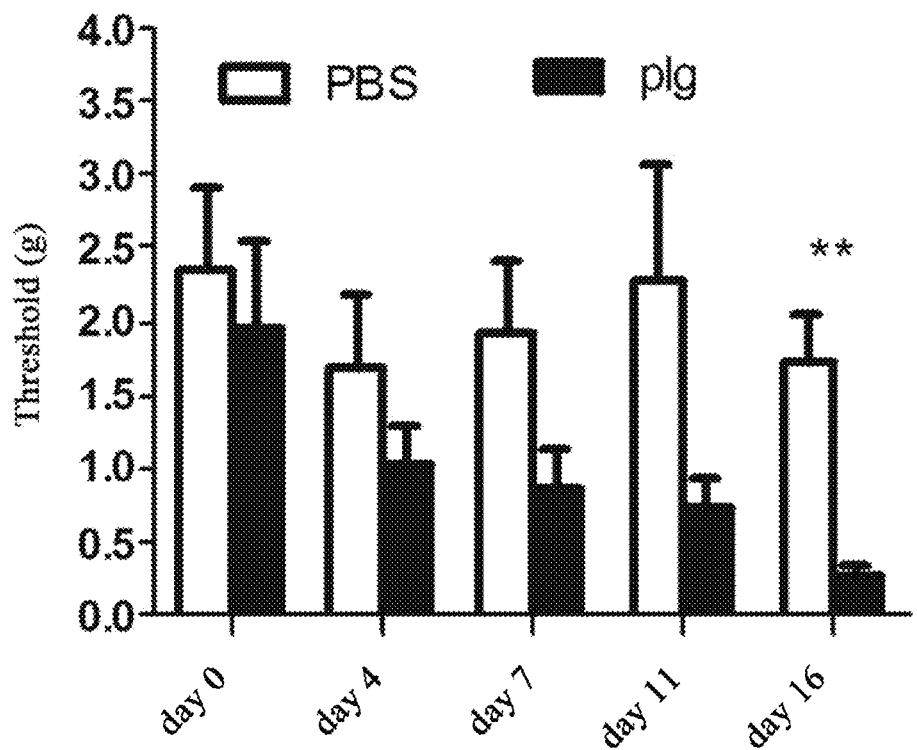
FIG. 12 shows the detection results of the ability to respond to mechanical allodynia on days 0, 4, 7, 11 and 16 after administration of plasminogen to 24-25-week-old db/db mice. The detection on day 16 shows that mice in the group administered with plasminogen were found to have an extremely significant difference in 50% algesia threshold as compared with those in the control group administered with vehicle PBS.

The study found that compared with mice in the control group administered with vehicle PBS, mice in the group administered with plasminogen showed uniform increase in the response to mechanical allodynia, and an extremely significant difference was found on day 16 compared with mice in the control group administered with vehicle PBS (FIG. 12), indicating that plasminogen can repair the ability of mice with nerve injury to respond to mechanical allodynia.

Example 13. Plasminogen Repairs Response of Mice with Nerve Injury to Cold Stimulation Ten male db/db mice aged 24-25 weeks were randomly divided into two groups, five in the control group administered with vehicle PBS and five in the group administered with plasminogen, respectively. The day when the experiment began was recorded on Day 0, the mice were weighed and grouped, and the physiological experiment was initiated. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration, a drop of acetone was squeezed out with a needleless syringe and the planta of each db/db mouse was slightly touched to cover the entire planta with acetone. Starting from the left foot, the left and right feet were stimulated alternately every 3 minutes for a total of 10 stimulations, and the number of paw withdrawals was counted. Percentage of response=number of paw withdrawals/number of stimulations×100%.

Figure 13:
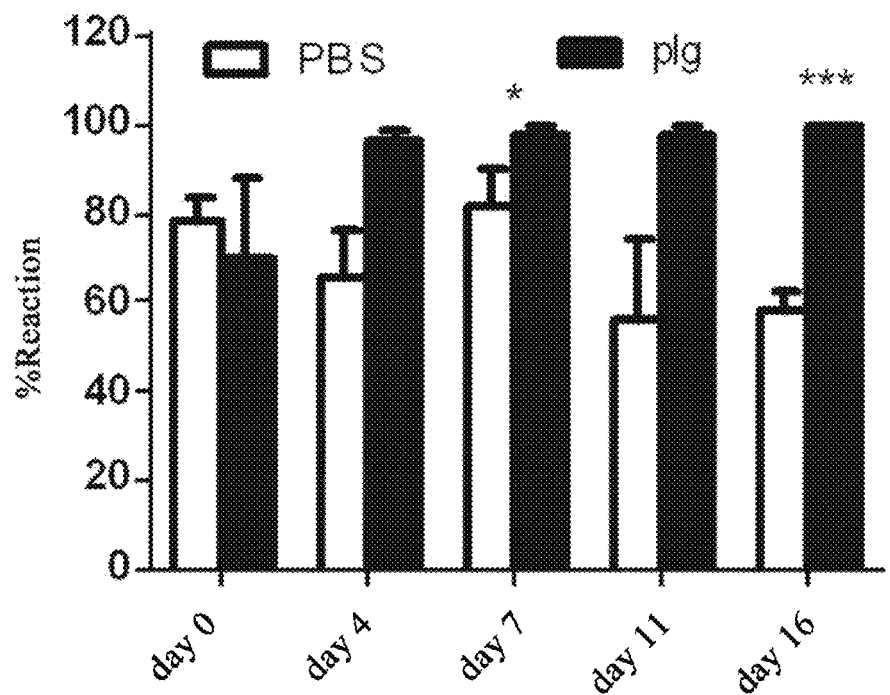
FIG. 13 shows the detection results of the ability to respond to cold stimulation on days 0, 4, 7, 11 and 16 after administration of plasminogen to 24-25-week-old db/db mice.

The experimental results showed that there was no significant difference in the response to acetone stimulation between mice in the group administered with plasminogen and those in the control group administered with vehicle PBS on days 0 and 4; however, a significant difference was observed from day 7, and an extremely significant difference was observed on day 16, and the P value was <0.0001 (FIG. 13), indicating that after 15 days of administration, the mice almost completely restored response to cold stimulation, suggesting that plasminogen can repair the ability of mice with nerve injury to respond to cold stimulation.

Example 14. Plasminogen Reduces the Fibrin Level in Nerve Tissues of Mice with Nerve Injury Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 16, and sciatic nerves were fixed in 10% neutral formalin fix solution for 24 hours. The fixed sciatic nerves were paraffin-embedded after dehydration with alcohol gradient and permeabilization with xylene. The thickness of the tissue sections was 5 μm. The sections were dewaxed and rehydrated and washed with water once, and then the tissues were circled with a PAP pen. The sections were incubated with hydrogen peroxide diluted with 3% TBS for 15 minutes, and washed with water three times. The sections were blocked with 10% normal goat serum (Vector laboratories, Inc., USA) for 1 hour, and excess serum was aspirated. The sections were incubated with rabbit anti-mouse fibrin (fibrinogen) antibody (Abcam) for 1 hour at room temperature or overnight at 4° C. and washed with TBS three times. The sections were incubated with a secondary antibody, goat anti-rabbit IgG (HRP) antibody (Abcam), for 1 hour at room temperature and washed with TBS three times. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Fibrinogen is the precursor of fibrin, and in the presence of tissue injury, as a stress response to the body's injury, fibrinogen is hydrolyzed into fibrin[22-24]. Therefore, fibrin levels can be used as a sign of the degree of injury. Fibrin is also the main component of thrombosis after tissue is injured. Therefore, fibrin levels can also be used as a marker of thrombi.

Figure 14:
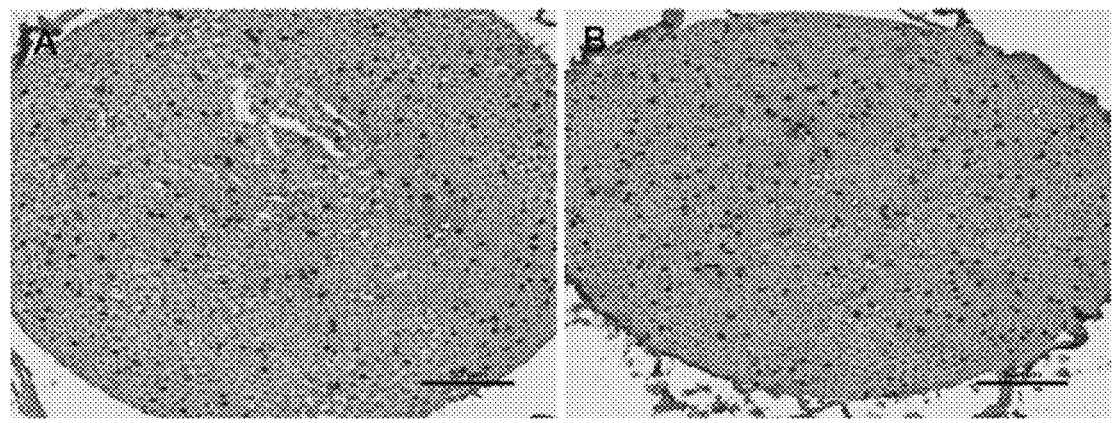
FIG. 14 shows the observed results of fibrin immumohistochemical staining of the sciatic nerve after administration of plasminogen to 24-25-week-old mice with nerve injury for 15 consecutive days.

The study found that compared with mice in the control group administered with vehicle PBS (FIG. 14A), those in the group administered with plasminogen (FIG. 14B) had a decreased level of fibrin in the sciatic nerve, indicating that plasminogen has the function of degrading fibrin level and the injury has been repaired to a certain degree, and also indicating that plasminogen can promote the dissolution of thrombi around nerve tissues.

Example 15. Plasminogen Alleviates the Injury of the Kidneys in Mice

Eight male db/db mice aged 24-25 weeks were randomly divided into two groups, four in the control group administered with vehicle PBS and four in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Detection of physiological indexes was finished on day 32, mice were sacrificed, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were incubated with goat anti-mouse IgM (HRP) antibody (Abcam) for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

IgM antibodies play an important role during the clearance of apoptotic and necrotic cells. The more apoptotic and necrotic cells are, the higher the local IgM antibody level is[29-31]. Therefore, local IgM antibody levels can reflect the injury of tissues and organs.

Figure 15:
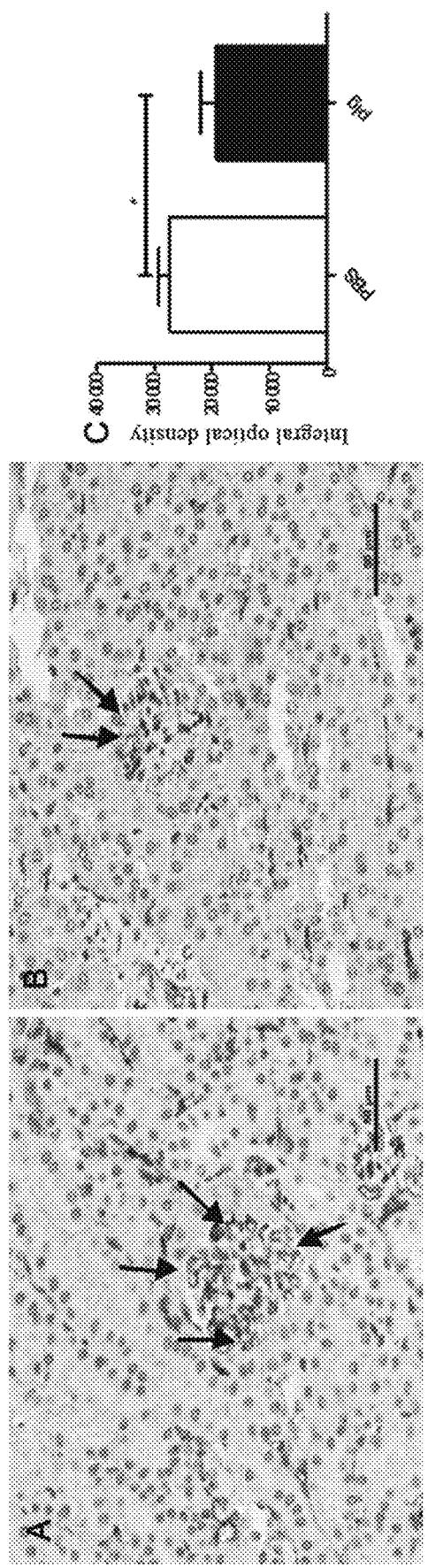
FIG. 15 shows the observed results of IgM immunostaining of the kidneys after administration of plasminogen to 24-25-week-old mice for 31 days.

The results showed that the positive staining of glomerular IgMs in mice in the group administered with plasminogen (FIG. 15B) was lighter than that of glomerular IgMs in mice in the control group administered with vehicle PBS (FIG. 15A), the range was also smaller than the control group, and the statistical analysis results were consistent with the observations (FIG. 15C), indicating that the glomerular injury is remarkably improved after injection of plasminogen, reflecting the significant protection and repair effects of plasminogen on the body's injury of mice.

Example 16. Plasminogen Promotes the Repair of Liver Injury of Mice

Nine male db/db mice aged 25-28 weeks were randomly divided into two groups, three in the control group administered with vehicle PBS and six in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Whole blood was taken from the removed eyeballs 31 days after administration of plasminogen. After the serum was precipitated, it was centrifuged at 3500 r/min for 10 minutes at 4° C., and the supernatant was taken for detection. In this experiment, the content of alanine transaminase (ALT) in serum was detected by Reitman-Frankel colorimetry using an alanine transaminase detection kit (Nanjing Jiancheng Biological Engineering Research Institute, Catalog No. C009-2).

Figure 16:
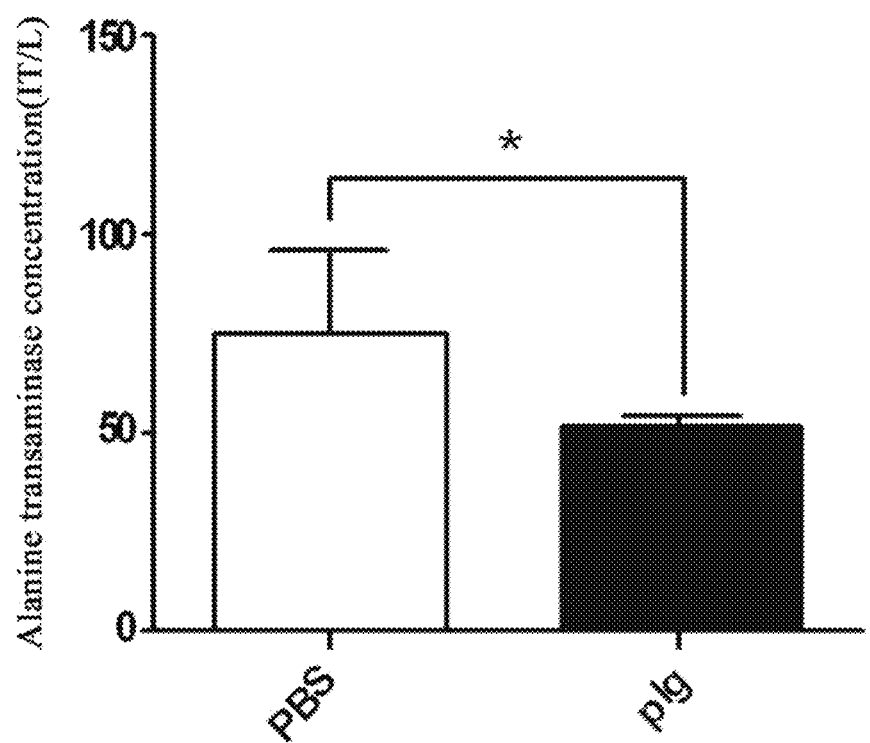
FIG. 16 shows the detection results of alanine transaminase (ALT) in serum after administration of plasminogen to 24-25-week-old mice for 31 days.

Alanine transaminase is an important index of liver health status[32,33], and the normal reference value interval of alanine transaminase is 9-50 U/L. The detection results showed that the ALT content in serum of mice in the control group administered with vehicle PBS was significantly higher than the normal physiological index, whereas the content in mice in the group administered with plasminogen had returned to normal levels in the body; and the ALT content in mice in the group administered with plasminogen was significantly lower than that in mice in the control group administered with vehicle PBS, and there was a statistical difference (FIG. 16). It shows that injection of plasminogen can obviously repair liver injury in model mice.

REFERENCES

[1] Alexander C M and Werb, Z. (1991). Extracellular matrix degradation. In Cell Biology of Extracellular Matrix, Hay E D, ed. (New York: Plenum Press), pp. 255-302

[2] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.

[3] He, C. S., Wilhelm, S. M., Pentland, A. P., Marmer, B. L., Grant, G A., Eisen, A. Z., and Goldberg, G I. (1989). Tissue cooperation in a proteolytic cascade activating human interstitial collagenase. Proc. Natl. Acad. Sci. U.S.A 86, 2632-2636

[4] Stoppelli, M. P., Corti, A., Soffientini, A., Cassani, G, Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U.S.A 82, 4939-4943.

[5] Vassalli, J. D., Baccino, D., and Belin, D. (1985). A cellular binding site for the Mr 55, 000 form of the human plasminogen activator, urokinase. J. Cell Biol. 100, 86-92.

[6] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[7] Saksela, O. and Rifkin, D. B. (1988). Cell-associated plasminogen activation: regulation and physiological functions. Annu. Rev. Cell Biol. 4, 93-126

[8] Raum, D., Marcus, D., Alper, C. A., Levey, R., Taylor, P. D., and Starzl, T. E. (1980). Synthesis of human plasminogen by the liver. Science 208, 1036-1037

[9] Wallén P (1980). Biochemistry of plasminogen. In Fibrinolysis, Kline D L and Reddy K K N, eds. (Florida: CRC

[10] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U.S.A 72, 2577-2581.

[11] Collen, D. and Lijnen, H. R. (1991). Basic and clinical aspects of fibrinolysis and thrombolysis. Blood 78, 3114-3124.

[12] Alexander, C. M. and Werb, Z. (1989). Proteinases and extracellular matrix remodeling. Curr. Opin. Cell Biol. 1, 974-982.

[13] Mignatti, P. and Rifkin, D. B. (1993). Biology and biochemistry of proteinases in tumor invasion. Physiol Rev. 73, 161-195.

[14] Collen, D. (2001). Ham-Wasserman lecture: role of the plasminogen system in fibrin-homeostasis and tissue remodeling. Hematology. (Am. Soc. Hematol. Educ. Program) 1-9.

[15] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[16] Andreasen, P. A., Kjoller, L., Christensen, L., and Duffy, M. J. (1997). The urokinase-type plasminogen activator system in cancer metastasis: a review. Int. J. Cancer 72, 1-22.

[17] Rifkin, D. B., Mazzieri, R., Munger, J. S., Noguera, I., and Sung, J. (1999). Proteolytic control of growth factor availability. APMIS 107, 80-85.

[18] Marder V J, Novokhatny V. Direct fibrinolytic agents: biochemical attributes, preclinical foundation and clinical potential [J]. Journal of Thrombosis and Haemostasis, 2010, 8(3): 433-444.

[19] Hunt J A, Petteway Jr S R, Scuderi P, et al. Simplified recombinant plasmin: production and functional comparison of a novel thrombolytic molecule with plasma-derived plasmin [J]. Thromb Haemost, 2008, 100(3): 413-419.

[20] Sottrup-Jensen L, Claeys H, Zajdel M, et al. The primary structure of human plasminogen: Isolation of two lysine-binding fragments and one "mini"-plasminogen (MW, 38, 000) by elastase-catalyzed-specific limited proteolysis [J]. Progress in chemical fibrinolysis and thrombolysis, 1978, 3: 191-209.

[21] Nagai N, Demarsin E, Van Hoef B, et al. Recombinant human microplasmin: production and potential therapeutic properties [J]. Journal of Thrombosis and Haemostasis, 2003, 1(2): 307-313.

[22] Jae Kyu Ryu, Mark A. Petersen, Sara G. Murray et al. Blood coagulation protein fibrinogen promotes autoimmunity and demyelination via chemokine release and antigen presentation. NATURE COMMUNICATIONS, 2015, 6:8164.

[23] Dimitrios Davalos, Katerina Akassoglou. Fibrinogen as a key regulator of inflammation in disease. Seminars in Immunopathology, 2012. 34(1):43-62.

[24] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.

[25] R. Langhorn and J. L. Willesen. Cardiac Troponins in Dogs and Cats. J Vet Intern Med 2016; 30:36-50.

[26] Moungjaroen J, Nimmannit U, Callery P S, Wang L, Azad N, Lipipun V, Chanvorachote P, Rojanasakul Y (2006). Reactive oxygen species mediate caspase activation and apoptosis induced by lipoic acid in human lung epithelial cancer cells through Bcl-2 downregulation. J Pharmacol Exp Ther 319, 1062-1069.

[27] Wang L, Chanvorachote P, Toledo D, Stehlik C, Mercer R R, Castranova V, Rojanasakul Y (2008). Peroxide is a key mediator of Bcl-2 down-regulation and apoptosis induction by cisplatinin human lung cancer cells. Mol Pharmacol 73, 119-127.
[28] S. R. Chaplan et al. Quantitative assessment of tactile allodynia in the rat paw, Journal of Neuroscience Methods 53 (1994) 55-63.
[29] Zwart B, Ciurana C, Rensink I, Manoe R, Hack C E, et al. (2004) Complement activation by apoptotic cells occurs predominantly via IgM and is limited to late apoptotic (secondary necrotic) cells. Autoimmunity 37: 95-102.
[30] Zhang M, Takahashi K, Alicot E M, Vorup-Jensen T, Kessler B, et al. (2006) Activation of the lectin pathway by natural IgM in a model of ischemia/reperfusion injury. J Immunol 177: 4727-4734.
[31] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.
[32] Karmen A, Wroblewski F, Ladue J S (January 1955). Transaminase activity in human blood. The Journal of Clinical Investigation. 34 (1): 126-31.
[33] Wang C S, Chang T F, Yao W J, Wang S T, Chou P (April 2012). Impact of increasing alanine aminotransferase levels within normal range on incident diabetes. Journal of the Formosan Medical Association=Taiwan Yi Zhi. 111 (4): 201-8

The invention claimed is:

1. A method for preventing and/or treating angiopathy in a subject, comprising administering an effective amount of plasminogen to the subject, wherein the angiopathy comprises atherosclerosis.

2. A method for preventing and/or treating angiocardiopathy in a subject, comprising administering an effective amount of plasminogen to the subject, wherein the angiocardiopathy comprises diabetic angiocardiopathy.

3. The method of claim 2, wherein the diabetic angiocardiopathy is caused by diabetes mellitus-induced angiopathy of large vessels, small vessels, and microvessels.

4. The method according to claim 1, wherein the plasminogen is a protein having at least 80%, 85%, 90%, 95%, 96%, 97%, 98% or 99% sequence identity with SEQ ID No. 2.

5. The method according to claim 1, wherein the plasminogen can be administered in combination with one or more other drugs.

6. The method of claim 5, wherein the other drugs comprise: anti-anginal drugs, anti-hyperlipidemic drugs, anti-hypertensive drugs, anti-inflammatory drugs, anti-infective drugs, aldosterone antagonists, blood glucose regulators, insulin, and anti-thrombotic drugs.

* * * * *

SEQUENCE LISTING

<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      human plasminogen(Glu-PLG,Glu-plasminogen) without the
      signal peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa aatttccaag     540
accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact tgtgacatc      720 ccccgctgca acacacctcc accatcttct ggtcccacct accagtgtct gaagggaaca     780
ggtgaaaact atcgcgggaa tgtggctgtt accgtgtccg ggcacacctg tcagcactgg     840
agtgcacaga cccctcacac acataacagg acaccagaaa acttccctg caaaaatttg    900 gatgaaaact actgccgcaa tcctgacgga aaagggccc catggtgcca tacaaccaac     960
agccaagtgc ggtgggagta ctgtaagata ccgtcctgtg actcctcccc agtatccacg    1020
gaacaattgg ctcccacagc accacctgag ctaaccctg tggtccagga ctgctaccat    1080
ggtgatggac agagctaccg aggcacatcc tccaccacca cacaggaaa gaagtgtcag    1140 tcttggtcat ctatgacacc acaccggcac cagaagaccc cagaaaacta cccaaatgct    1200
ggcctgacaa tgaactactg caggaatcca gatgccgata aggcccctg gtgttttacc    1260 acagacccca gcgtcaggtg ggagtactgc aacctgaaaa aatgctcagg aacagaagcg    1320

```
agtgttgtag cacctccgcc tgttgtcctg cttccagatg tagagactcc ttccgaagaa   1380
gactgtatgt ttgggaatgg gaaaggatac cgaggcaaga gggcgaccac tgttactggg   1440
acgccatgcc aggactgggc tgcccaggag ccccatagac acagcatttt cactccagag   1500
acaaatccac gggcgggtct ggaaaaaaat tactgccgta accctgatgg tgatgtaggt   1560
ggtccctggt gctacacgac aaatccaaga aaactttacg actactgtga tgtccctcag   1620
tgtgcggccc cttcatttga ttgtgggaag cctcaagtgg agccgaagaa atgtcctgga   1680
agggttgtag gggggtgtgt ggcccaccca cattcctggc cctggcaagt cagtcttaga   1740
acaaggtttg gaatgcactt ctgtggaggc accttgatat ccccagagtg ggtgttgact   1800
gctgcccact gcttggagaa gtccccaagg ccttcatcct acaaggtcat cctgggtgca   1860
caccaagaag tgaatctcga accgcatgtt caggaaatag aagtgtctag gctgttcttg   1920
gagcccacac gaaaagatat tgccttgcta aagctaagca gtcctgccgt catcactgac   1980
aaagtaatcc cagcttgtct gccatcccca aattatgtgg tcgctgaccg gaccgaatgt   2040
ttcatcactg gctggggaga aacccaaggt acttttggag ctggccttct caaggaagcc   2100
cagctccctg tgattgagaa taaagtgtgc aatcgctatg agtttctgaa tggaagagtc   2160
caatccaccg aactctgtgc tgggcatttg gccggaggca ctgacagttg ccagggtgac   2220
agtggaggtc ctctggtttg cttcgagaag gacaaataca ttttacaagg agtcacttct   2280
tggggtcttg gctgtgcacg ccccaataag cctggtgtct atgttcgtgt ttcaaggttt   2340
gttacttgga ttgagggagt gatgagaaat aattaa                            2376
```

<210> SEQ ID NO 2
<211> LENGTH: 791
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of the natural human
      plasminogen(Glu-PLG,Glu-plasminogen)without the
      signal peptide

<400> SEQUENCE: 2

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
            165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
        210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
        290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
        340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
        370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Val
        435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
        530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln

```
                  565                 570                 575
    Val Ser Leu Arg Thr Arg Phe Gly Met His Phe Cys Gly Gly Thr Leu
                580                 585                 590

Ile Ser Pro Glu Trp Val Leu Thr Ala Ala His Cys Leu Glu Lys Ser
                595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
    625                 630                 635                 640

Glu Pro Thr Arg Lys Asp Ile Ala Leu Leu Lys Leu Ser Ser Pro Ala
                    645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
                    675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
    705                 710                 715                 720

Gln Ser Thr Glu Leu Cys Ala Gly His Leu Ala Gly Gly Thr Asp Ser
                    725                 730                 735

Cys Gln Gly Asp Ser Gly Gly Pro Leu Val Cys Phe Glu Lys Asp Lys
                740                 745                 750

Tyr Ile Leu Gln Gly Val Thr Ser Trp Gly Leu Gly Cys Ala Arg Pro
                    755                 760                 765

Asn Lys Pro Gly Val Tyr Val Arg Val Ser Arg Phe Val Thr Trp Ile
            770                 775                 780

Glu Gly Val Met Arg Asn Asn
    785                 790

<210> SEQ ID NO 3
<211> LENGTH: 2433
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for the natural
      plasminogen (from swiss prot)with the signal peptide

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag gaagtataga agaatgtgca gcaaaatgtg aggaggacga agaattcacc     180
tgcagggcat tccaatatca cagtaaagag caacaatgtg tgataatggc tgaaaacagg     240
aagtcctcca taatcattag gatgagagat gtagttttat ttgaaaagaa agtgtatctc     300
tcagagtgca agactgggaa tggaagaaac tacagaggga cgatgtccaa aacaaaaaat     360
ggcatcacct gtcaaaaatg gagttccact tctccccaca gacctagatt ctcacctgct     420
acacacccct cagagggact ggaggagaac tactgcagga atccagacaa cgatccgcag     480 gggcctggt gctatactac tgatccagaa aagagatatg actactgcga cattcttgag      540
tgtgaagagg aatgtatgca ttgcagtgga gaaaactatg acggcaaaat ttccaagacc     600
atgtctggac tggaatgcca ggcctgggac tctcagagcc cacacgctca tggatacatt     660
```

```
cctccaaat ttccaaacaa gaacctgaag aagaattact gtcgtaaccc cgatagggag    720
ctgcggcctt ggtgtttcac caccgacccc aacaagcgct gggaactttg tgacatcccc    780
cgctgcacaa cacctccacc atcttctggt cccacctacc agtgtctgaa gggaacaggt    840
gaaaactatc gcgggaatgt ggctgttacc gtgtccgggc acacctgtca gcactggagt    900
gcacagaccc ctcacacaca taacaggaca ccagaaaact tccctgcaa aatttggat    960 gaaaactact gccgcaatcc tgacggaaaa agggccccat ggtgccatac aaccaacagc    1020
caagtgcggt gggagtactg taagataccg tcctgtgact cctccccagt atccacggaa    1080
caattggctc ccacagcacc acctgagcta accctgtgg tccaggactg ctaccatggt    1140
gatggacaga gctaccgagg cacatcctcc accaccacca caggaaagaa gtgtcagtct    1200
tggtcatcta tgacaccaca ccggcaccag aagaccccag aaaactaccc aaatgctggc    1260
ctgacaatga actactgcag gaatccagat gccgataaag gccctggtg ttttaccaca    1320 gaccccagcg tcaggtggga gtactgcaac ctgaaaaaat gctcaggaac agaagcgagt    1380
gttgtagcac ctccgcctgt tgtcctgctt ccagatgtag agactccttc gaagaagac    1440 tgtatgtttg ggaatgggaa aggataccga ggcaagaggg cgaccactgt tactgggacg    1500
ccatgccagg actgggctgc ccaggagccc catagacaca gcattttcac tccagagaca    1560
aatccacggg cggtctgga aaaaaattac tgccgtaacc ctgatggtga tgtaggtggt    1620
ccctggtgct acacgacaaa tccaagaaaa ctttacgact actgtgatgt ccctcagtgt    1680 gcggccccctt catttgattg tgggaagcct caagtggagc cgaagaaatg tcctggaagg    1740
gttgtagggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                 2433
```

<210> SEQ ID NO 4
<211> LENGTH: 810
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence coding for the natural
      plasminogen (from swiss prot)with the signal peptide

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser

```
            20                  25                  30
Leu Phe Ser Val Thr Lys Lys Gln Leu Gly Ala Gly Ser Ile Glu Glu
        35                  40                  45
Cys Ala Ala Lys Cys Glu Glu Asp Glu Glu Phe Thr Cys Arg Ala Phe
    50                  55                  60
Gln Tyr His Ser Lys Glu Gln Cys Val Ile Met Ala Glu Asn Arg
 65                  70                  75                  80
Lys Ser Ser Ile Ile Ile Arg Met Arg Asp Val Val Leu Phe Glu Lys
                85                  90                  95
Lys Val Tyr Leu Ser Glu Cys Lys Thr Gly Asn Gly Lys Asn Tyr Arg
            100                 105                 110
Gly Thr Met Ser Lys Thr Lys Asn Gly Ile Thr Cys Gln Lys Trp Ser
            115                 120                 125
Ser Thr Ser Pro His Arg Pro Arg Phe Ser Pro Ala Thr His Pro Ser
            130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Glu Cys Met His Cys Ser Gly Glu Asn
            180                 185                 190
Tyr Asp Gly Lys Ile Ser Lys Thr Met Ser Gly Leu Glu Cys Gln Ala
            195                 200                 205
Trp Asp Ser Gln Ser Pro His Ala His Gly Tyr Ile Pro Ser Lys Phe
            210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
            290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
            355                 360                 365
Glu Leu Thr Pro Val Val Gln Asp Cys Tyr His Gly Asp Gly Gln Ser
            370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
            435                 440                 445
```

```
Cys Asn Leu Lys Lys Cys Ser Gly Thr Glu Ala Ser Val Val Ala Pro
    450                 455                 460
Pro Pro Val Val Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
His Ser Ile Phe Thr Pro Glu Thr Asn Pro Arg Ala Gly Leu Glu Lys
        515                 520                 525
Asn Tyr Cys Arg Asn Pro Asp Gly Asp Val Gly Gly Pro Trp Cys Tyr
    530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                565                 570                 575
Cys Pro Gly Arg Val Val Gly Gly Cys Val Ala His Pro His Ser Trp
            580                 585                 590
Pro Trp Gln Val Ser Leu Arg Thr Arg Phe Gly Met His Phe Cys Gly
        595                 600                 605
Gly Thr Leu Ile Ser Pro Glu Trp Val Leu Thr Ala Ala His Cys Leu
    610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
                645                 650                 655
Leu Phe Leu Glu Pro Thr Arg Lys Asp Ile Ala Leu Leu Lys Leu Ser
            660                 665                 670
Ser Pro Ala Val Ile Thr Asp Lys Val Ile Pro Ala Cys Leu Pro Ser
        675                 680                 685
Pro Asn Tyr Val Val Ala Asp Arg Thr Glu Cys Phe Ile Thr Gly Trp
    690                 695                 700
Gly Glu Thr Gln Gly Thr Phe Gly Ala Gly Leu Leu Lys Glu Ala Gln
705                 710                 715                 720
Leu Pro Val Ile Glu Asn Lys Val Cys Asn Arg Tyr Glu Phe Leu Asn
                725                 730                 735
Gly Arg Val Gln Ser Thr Glu Leu Cys Ala Gly His Leu Ala Gly Gly
            740                 745                 750
Thr Asp Ser Cys Gln Gly Asp Ser Gly Gly Pro Leu Val Cys Phe Glu
        755                 760                 765
Lys Asp Lys Tyr Ile Leu Gln Gly Val Thr Ser Trp Gly Leu Gly Cys
    770                 775                 780
Ala Arg Pro Asn Lys Pro Gly Val Tyr Val Arg Val Ser Arg Phe Val
785                 790                 795                 800
Thr Trp Ile Glu Gly Val Met Arg Asn Asn
                805                 810

<210> SEQ ID NO 5
<211> LENGTH: 2145
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Nucleotide sequence coding for
      LYS77-PLG(Lys-plasminogen)

<400> SEQUENCE: 5

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |
| ttctcacctg | ctacacaccc | ctcagaggga | ctggaggaga | actactgcag | gaatccagac | 180 |
| aacgatccgc | aggggccctg | gtgctatact | actgatccag | aaaagagata | tgactactgc | 240 |
| gacattcttg | agtgtgaaga | ggaatgtatg | cattgcagtg | gagaaaacta | tgacggcaaa | 300 |
| atttccaaga | ccatgtctgg | actggaatgc | caggcctggg | actctcagag | cccacacgct | 360 |
| catggataca | ttccttccaa | atttccaaac | aagaacctga | agaagaatta | ctgtcgtaac | 420 |
| cccgataggg | agctgcggcc | ttggtgtttc | accaccgacc | ccaacaagcg | ctgggaactt | 480 |
| tgtgacatcc | cccgctgcac | aacacctcca | ccatcttctg | gtcccaccta | ccagtgtctg | 540 |
| aagggaacag | gtgaaaacta | tcgcgggaat | gtggctgtta | ccgtgtccgg | gcacacctgt | 600 |
| cagcactgga | gtgcacagac | ccctcacaca | cataacagga | caccagaaaa | cttcccctgc | 660 |
| aaaaatttgg | atgaaaacta | ctgccgcaat | cctgacggaa | aaaggccccc | atggtgccat | 720 |
| acaaccaaca | gccaagtgcg | gtgggagtac | tgtaagatac | cgtcctgtga | ctcctcccca | 780 |
| gtatccacgg | aacaattggc | tcccacagca | ccacctgagc | taaccctgt | ggtccaggac | 840 |
| tgctaccatg | gtgatggaca | gagctaccga | ggcacatcct | ccaccaccac | cacaggaaag | 900 |
| aagtgtcagt | cttggtcatc | tatgacacca | caccggcacc | agaagacccc | agaaaactac | 960 |
| ccaaatgctg | gcctgacaat | gaactactgc | aggaatccag | atgccgataa | aggcccctgg | 1020 |
| tgttttacca | cagaccccag | cgtcaggtgg | gagtactgca | acctgaaaaa | atgctcagga | 1080 |
| acagaagcga | gtgttgtagc | acctccgcct | gttgtcctgc | ttccagatgt | agagactcct | 1140 |
| tccgaagaag | actgtatgtt | tgggaatggg | aaaggatacc | gaggcaagag | ggcgaccact | 1200 |
| gttactggga | cgccatgcca | ggactgggct | gcccaggagc | cccatagaca | cagcattttc | 1260 |
| actccagaga | caaatccacg | gcgggtctg | gaaaaaaatt | actgccgtaa | ccctgatggt | 1320 |
| gatgtaggtg | gtccctggtg | ctacacgaca | aatccaagaa | aactttacga | ctactgtgat | 1380 |
| gtccctcagt | gtgcggcccc | ttcatttgat | tgtgggaagc | ctcaagtgga | gccgaagaaa | 1440 |
| tgtcctggaa | gggttgtagg | ggggtgtgtg | gcccacccac | attcctggcc | ctggcaagtc | 1500 |
| agtcttagaa | caaggtttgg | aatgcacttc | tgtggaggca | ccttgatatc | cccagagtgg | 1560 |
| gtgttgactg | ctgcccactg | cttggagaag | tccccaaggc | cttcatccta | caaggtcatc | 1620 |
| ctgggtgcac | accaagaagt | gaatctcgaa | ccgcatgttc | aggaaataga | agtgtctagg | 1680 |
| ctgttcttgg | agcccacacg | aaaagatatt | gccttgctaa | agctaagcag | tcctgccgtc | 1740 |
| atcactgaca | aagtaatccc | agcttgtctg | ccatccccaa | attatgtggt | cgctgaccgg | 1800 |
| accgaatgtt | tcatcactgg | ctggggagaa | acccaaggta | cttttggagc | tggccttctc | 1860 |
| aaggaagccc | agctccctgt | gattgagaat | aaagtgtgca | atcgctatga | gtttctgaat | 1920 |
| ggaagagtcc | aatccaccga | actctgtgct | gggcatttgg | ccggaggcac | tgacagttgc | 1980 |
| cagggtgaca | gtggaggtcc | tctggtttgc | ttcgagaagg | acaaatacat | tttacaagga | 2040 |
| gtcacttctt | ggggtcttgg | ctgtgcacgc | cccaataagc | ctggtgtcta | tgttcgtgtt | 2100 |
| tcaaggtttg | ttacttggat | tgagggagtg | atgagaaata | attaa | 2145 |

<210> SEQ ID NO 6

```
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of
      LYS77-PLG(Lys-plasminogen)

<400> SEQUENCE: 6

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
```

```
                    355                 360                 365
Pro Pro Val Leu Leu Pro Asp Val Glu Thr Pro Ser Glu Glu Asp
370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
        435                 440                 445

Thr Thr Asn Pro Arg Lys Leu Tyr Asp Tyr Cys Asp Val Pro Gln Cys
    450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for
      delta-plg(delta-plasminogen)
```

<400> SEQUENCE: 7

```
gagcctctgg atgactatgt gaataccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag gacgatgtc caaaacaaaa      300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaagagat atgactactg cgacattctt      480
gagtgtgaag aggcggcccc ttcatttgat tgtgggaagc ctcaagtgga gccgaagaaa     540
tgtcctggaa gggttgtagg ggggtgtgtg gcccaccac attcctggcc ctggcaagtc      600
agtcttagaa caaggtttgg aatgcacttc tgtggaggca ccttgatatc cccagagtgg     660
gtgttgactg ctgcccactg cttggagaag tccccaaggc cttcatccta caaggtcatc     720
ctgggtgcac accaagaagt gaatctcgaa ccgcatgttc aggaaataga agtgtctagg     780
ctgttcttgg agcccacacg aaaagatatt gccttgctaa agctaagcag tcctgccgtc     840
atcactgaca agtaatccc agcttgtctg ccatccccaa attatgtggt cgctgaccgg     900
accgaatgtt tcatcactgg ctggggagaa acccaaggta cttttggagc tggccttctc     960
aaggaagccc agctccctgt gattgagaat aaagtgtgca atcgctatga gtttctgaat    1020
ggaagagtcc aatccaccga actctgtgct gggcatttgg ccggaggcac tgacagttgc    1080
cagggtgaca gtggaggtcc tctggtttgc ttcgagaagg acaaatacat tttacaagga    1140
gtcacttctt ggggtcttgg ctgtgcacgc cccaataagc ctggtgtcta tgttcgtgtt    1200
tcaaggtttg ttacttggat tgagggagtg atgagaaata attaa                    1245
```

<210> SEQ ID NO 8
<211> LENGTH: 414
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence of delta-plg(delta-plasminogen)

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110
```

```
Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
        180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
        260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
        340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410

<210> SEQ ID NO 9
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for
      Mini-plg(mini-plasminogen)

<400> SEQUENCE: 9
gtcaggtggg agtactgcaa cctgaaaaaa tgctcaggaa cagaagcgag tgttgtagca    60
cctccgcctg ttgtcctgct tccagatgta gagactcctt ccgaagaaga ctgtatgttt   120
gggaatggga aagataccg aggcaagagg gcgaccactt tactgggac gccatgccag    180 gactgggctg cccaggagcc ccatagacac agcattttca ctccagagac aaatccacgg   240
```

-continued

```
gcgggtctgg aaaaaaatta ctgccgtaac cctgatggtg atgtaggtgg tccctggtgc      300
tacacgacaa atccaagaaa actttacgac tactgtgatg tccctcagtg tgcggcccct      360
tcatttgatt gtgggaagcc tcaagtggag ccgaagaaat gtcctggaag ggttgtaggg      420
gggtgtgtgg cccacccaca ttcctggccc tggcaagtca gtcttagaac aaggtttgga      480
atgcacttct gtggaggcac cttgatatcc ccagagtggg tgttgactgc tgcccactgc      540
ttggagaagt ccccaaggcc ttcatcctac aaggtcatcc tgggtgcaca ccaagaagtg      600
aatctcgaac cgcatgttca ggaaatagaa gtgtctaggc tgttcttgga gcccacacga      660
aaagatattg ccttgctaaa gctaagcagt cctgccgtca tcactgacaa agtaatccca      720
gcttgtctgc atccccaaa ttatgtggtc gctgaccgga ccgaatgttt catcactggc      780
tggggagaaa cccaaggtac ttttggagct ggccttctca aggaagccca gctccctgtg      840
attgagaata aagtgtgcaa tcgctatgag tttctgaatg gaagagtcca atccaccgaa      900
ctctgtgctg gcatttggc cggaggcact gacagttgcc agggtgacag tggaggtcct      960
ctggtttgct tcgagaagga caaatacatt ttacaaggag tcacttcttg gggtcttggc     1020
tgtgcacgcc ccaataagcc tggtgtctat gttcgtgttt caaggtttgt tacttggatt     1080
gagggagtga tgagaaataa ttaa                                             1104
```

<210> SEQ ID NO 10
<211> LENGTH: 367
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: Amino acid sequence of
       Mini-plg(mini-plasminogen)

<400> SEQUENCE: 10

```
Val Arg Trp Glu Tyr Cys Asn Leu Lys Lys Cys Ser Gly Thr Glu Ala
1               5                  10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
    50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
    130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
```

```
                180             185             190
Ile Leu Gly Ala His Gln Glu Val Asn Leu Glu Pro His Val Gln Glu
            195                 200                 205

Ile Glu Val Ser Arg Leu Phe Leu Glu Pro Thr Arg Lys Asp Ile Ala
            210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
            275                 280                 285

Tyr Glu Phe Leu Asn Gly Arg Val Gln Ser Thr Glu Leu Cys Ala Gly
            290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
            355                 360                 365
```

<210> SEQ ID NO 11
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence coding for
      Micro-plg(micro-plasminogen)

<400> SEQUENCE: 11

```
gcccttcat ttgattgtgg aagcctcaa gtggagccga agaaatgtcc tggaagggtt      60
gtaggggggt gtgtggccca cccacattcc tggccctggc aagtcagtct tagaacaagg    120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttgggt    660 cttggctgtg cacgccccaa taagcctggt gtctatgttc gtgtttcaag gtttgttact    720
tggattgagg gagtgatgag aaataattaa                                      750
```

<210> SEQ ID NO 12
<211> LENGTH: 249
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence coding for Micro-plg(micro-plasminogen)

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotide sequence coding for the serine protease domain

<400> SEQUENCE: 13
gttgtagggg ggtgtgtggc ccacccacat tcctggccct ggcaagtcag tcttagaaca      60
aggtttggaa tgcacttctg tggaggcacc ttgatatccc cagagtgggt gttgactgct     120
gcccactgct tggagaagtc cccaaggcct tcatcctaca aggtcatcct gggtgcacac     180
caagaagtga atctcgaacc gcatgttcag gaaatagaag tgtctaggct gttcttggag     240

```
cccacacgaa aagatattgc cttgctaaag ctaagcagtc ctgccgtcat cactgacaaa    300
gtaatcccag cttgtctgcc atccccaaat tatgtggtcg ctgaccggac cgaatgtttc    360
atcactggct ggggagaaac ccaaggtact tttggagctg gccttctcaa ggaagcccag    420
ctccctgtga ttgagaataa agtgtgcaat cgctatgagt ttctgaatgg aagagtccaa    480
tccaccgaac tctgtgctgg gcatttggcc ggaggcactg acagttgcca gggtgacagt    540
ggaggtcctc tggtttgctt cgagaaggac aaatacattt tacaaggagt cacttcttgg    600
ggtcttggct gtgcacgccc caataagcct ggtgtctatg ttcgtgtttc aaggtttgtt    660
acttggattg agggagtgat gaga                                          684
```

<210> SEQ ID NO 14
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence coding for the serine
      protease domain

<400> SEQUENCE: 14

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225